(12) United States Patent
Abe et al.

(10) Patent No.: US 6,197,318 B1
(45) Date of Patent: Mar. 6, 2001

(54) COMPOSITION FOR EXTERNAL USE

(75) Inventors: Koji Abe; Reiji Miyahara; Tomiyuki Nanba; Tadashi Nakamura; Toshikatsu Hayashi; Nozomiko Seki, all of Kanagawa; Keiichi Uehara, Osaka; Syoji Nishiyama, Kanagawa, all of (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/341,146

(22) PCT Filed: Sep. 9, 1998

(86) PCT No.: PCT/JP98/04040
§ 371 Date: Jul. 16, 1999
§ 102(e) Date: Jul. 16, 1999

(87) PCT Pub. No.: WO99/26590
PCT Pub. Date: Jun. 3, 1999

(30) Foreign Application Priority Data

Nov. 20, 1997 (JP) .................................................. 9-337916

(51) Int. Cl.$^7$ .............................. A61K 7/00; A61K 7/42; A61K 35/78; A61K 47/00
(52) U.S. Cl. ............................. 424/401; 424/59; 424/60; 424/195.1; 424/197.1; 424/400; 514/783; 514/773; 514/777
(58) Field of Search .............................. 424/59, 60, 400, 424/407, 195.1, 197.1; 514/783, 773, 777

(56) References Cited

U.S. PATENT DOCUMENTS 5,403,599 * 4/1995 Whistler .................................. 426/48
5,547,997 * 8/1996 Kludas .................................. 514/773
5,876,729 * 3/1999 Pauly .................................. 424/195.1

* cited by examiner

Primary Examiner—Shelley A. Dodson
(74) Attorney, Agent, or Firm—Townsend & Banta

(57) ABSTRACT

A composition for external use which contains xyloglucan. It preferably further contains an ultraviolet shielding agent, a thickening polysaccharide, a thickening polysaccharide and sericin, a carboxyvinylpolymer, or an alkyl-modified carboxyvinylpolymer.

27 Claims, No Drawings

COMPOSITION FOR EXTERNAL USE

TECHNICAL FIELD

The present invention relates to a composition for external use, and more particularly, to a composition for external use which attains a variety of excellent characteristics through incorporation of xyloglucan, which is a polysaccharide originating from tamarind beans, as an essential ingredient.

BACKGROUND OF THE INVENTION

Conventionally, a variety of ingredients have been incorporated into a composition for external use, (hereinafter called an "external-use composition") such as a cosmetic composition, in accordance with the function to be realized in the external-use composition.

For example, an ultraviolet shielding agent is incorporated into an external-use composition in order to protect the skin from exposure to ultraviolet rays in sunlight, so as to prevent generation of age spots or freckles and skin aging, as well as to prevent generation of skin diseases such as skin cancer. When an external-use composition is processed into an emulsion such as milky lotion or cream or is stabilized, a surfactant is incorporated into the composition so as to emulsify or stabilize the composition.

Incorporation into an external-use composition of an ingredient suited for achieving an object enables provision of products matching a wide range of consumer needs; however, the incorporation may cause adverse effects.

Of the above examples, an external-use composition incorporated with an ultraviolet shielding agent tends to involve deteriorated sensation in use. Also, an external-use composition containing a surfactant in a large amount has been known to cause problems in safety and sensation in use.

A variety of measures have been investigated in attempts to solve the above-mentioned problems and to provide a higher quality, more reliable external-use composition.

Thus, a problem to be solved by the present invention is to find a key ingredient for effectively coping with the above problems, and to provide various external-use compositions in which the ingredient is used.

DISCLOSURE OF THE INVENTION

The present inventors have conducted earnest studies to solve the above-described problems, and have found that xyloglucan, which is a polysaccharide originating from a plant, can serve as the above-described key ingredient.

Xyloglucan which is incorporated into the external-use composition according to the present invention (hereinafter referred to as the external-use composition of the present invention) is a polysaccharide having a molecular weight of approximately 650,000 and is a predominant ingredient of beans of *Tamarindus indica,* a legume that mainly grows in tropical regions. Xyloglucan has a structure such that xylose and galactose form side chains and are bound to a main chain formed of β-1,4-glucan, and is represented by the following formula (I):

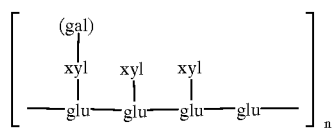

wherein glu represents a glucose unit; xyl represents a xylol unit; gal represents a galactose unit; and n represents the number of repeating units.

Xyloglucan is a Newtonian fluid having starch-like fluidity, and is sufficiently viscous that it gels when brought into contact with a sugar. In addition, xyloglucan has excellent stability against acid, heat, and salt, and excellent water retention.

Xyloglucan is now commercially available (trade name: GLYLOID, product of Dainippon Pharmaceutical Co., Ltd.), and is generally used as a thickener for food products such as Worcestershire sauce and ice cream.

When a commercial product of xyloglucan is incorporated into the external-use composition of the present invention, the product is preferably refined as finely as possible.

Xyloglucan may be produced by a method described in a catalog in which the above "GLYLOID" appears.

Specifically, the method comprises the steps of removing foreign matter from beans of tamarind; dipping the beans in water; crushing; removing impurities from the crushed product; washing and drying the crushed product; and finely crushing the dried product, to thereby obtain xyloglucan.

No particular limitation is imposed on the amount of xyloglucan incorporated into the external-use composition of the present invention; the amount varies in accordance with the specific mode of the composition and is appropriately selected in accordance with the specific product form and the form of commercial products. Amounts for specific modes of the composition will be described later.

Incorporation of xyloglucan into the external-use composition of the present invention and modifying the composition through any of a variety of methods yields an external-use composition having excellent characteristics not possessed by conventional compositions.

In the present invention, the term "external-use composition" broadly refers to a composition which may be applied to the outer skin (including the hair and the scalp), and is not limited by a legally defined concept; e.g., a cosmetic composition, drug, or quasi-drug.

BEST MODE FOR CARRYING OUT THE INVENTION

A. A first mode of the present invention is directed to an external-use composition in which both xyloglucan and ultraviolet shielding agents are incorporated (hereinafter the composition will be referred to as the "external-use composition of the first mode of the present invention").

Recently, ultraviolet rays in sunlight has been discovered to have severe, adverse effects on the human body, and skin care products that counter ultraviolet rays have become increasingly important.

In accordance with such a trend, in order to shield human skin from ultraviolet rays in sunlight, there have been developed many external-use compositions, such as cosmetics, which incorporate a variety of ultraviolet shielding agents.

In order to obtain a sufficient effect of protecting the skin from ultraviolet rays, ultraviolet shielding agents may be incorporated into an external-use composition in a large amount. However, among ultraviolet shielding agents, most ultraviolet absorbents, which mainly absorb ultraviolet rays chemically, are sticky, and when a large amount of the absorbers is incorporated into an external use composition, the absorbers may lead to an unpleasant sensation of the composition. In a product containing an ultraviolet scattering agent, which mainly scatters ultraviolet rays physically, the agent should be dispersed in more stable condition, since the agent may coagulate with passage of time and may markedly tend to impair the intended effect of the product.

Quite unexpectedly, the present inventors discovered the following: an external-use composition containing both xyloglucan and ultraviolet shielding agents does not have a sticky sensation in use when a large amount of ultraviolet absorbents (which are included in the category of ultraviolet shielding agents) is incorporated into the composition; ultraviolet scattering agents (which are a type of ultraviolet shielding agent) do not coagulate in the composition when a large amount thereof is incorporated; the ultraviolet shielding agents retain their effectiveness even after long-term storage in the composition; and these effects may be in particular improved when sugar-derived ultraviolet absorbents are incorporated in the composition, and led to completion of the present invention. Such a composition is called the "external-use composition of the first mode of the present invention."

Throughout the present specification, an "ultraviolet shielding agent" encompasses two concepts; an "ultraviolet absorbent," which mainly absorbs ultraviolet rays chemically, and an "ultraviolet scattering agent," which mainly scatters ultraviolet rays physically.

In the external-use composition of the first mode of the present invention, the amount of incorporated xyloglucan is 0.01–10.0 wt. %, preferably 0.1–4.0 wt. %, with respect to the entirety of the composition.

In the external-use composition of the first mode of the present invention, when the amount of incorporated xyloglucan is less than 0.01 wt. % with respect to the entirety of the composition, substantial difficulty is encountered in obtaining the intended effects; i.e., that the composition containing ultraviolet absorbents has improved sensation in use, and that ultraviolet scattering agents are dispersed in stable condition in the composition. When the incorporation amount thereof is more than 10.0 wt. % with respect to the entirety of the composition, xyloglucan forms a polymer film in the composition, which may lead to an unpleasant sensation in use.

Ultraviolet shielding agents incorporated together with xyloglucan into the external-use composition of the first mode of the present invention are not particularly limited, and the following ultraviolet shielding agents may be incorporated.

Examples of ultraviolet absorbents include p-aminobenzoate ultraviolet absorbents such as a p-aminobenzoic acid (hereinafter referred to as PABA), a PABA monoglycerin ester, an N,N-dipropoxy PABA ethyl ester, an N,N-diethoxy PABA ethyl ester, an N,N-dimethyl PABA ethyl ester, an N,N-dimethyl PABA butyl ester, and an N,N-dimethyl PABA methyl ester; anthranilate ultraviolet absorbents such as homomenthyl-N-acetyl anthranilate; salicylate ultraviolet absorbents such as amyl salicylate, menthyl salicylate, homomenthyl salicylate, octyl salicylate, phenyl salicylate, benzyl salicylate, and p-isopropanol phenyl salicylate; cinnamate ultraviolet absorbents such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glycerylmono-2-ethylhexanoyl diparamethoxycinnamate; benzophenone ultraviolet absorbents such as 2,4-dihydroxybenzophenone, 2,2'-dihydroxymethoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate salt, 4-phenylbenzophenone, 2-ethylhexyl-4'-phenylbenzophenone-2-carboxylate, 2-hydroxy-4-n-octoxybenzophenone, and 4-hydroxy-3-carboxybenzophenone; sugar-derived ultraviolet absorbents including a sugar-cinnamate derivative such as maltitol trimethoxycinnamate described in Japanese Patent Application Laid-open (kokai) No. 305592/1992 and a sugar benzophenone derivative such as 2-hydroxy-4-(2-β-glucopyranosiloxy) propoxybenzophenone described in Japanese Patent Application Laid-open (kokai) No. 87879/1994; 3-(4'-methylbenzylidene)-d-camphor; 3-benzylidene-d,l-camphor; urocanic acid; ethyl urocanate; 2-phenyl-5-methylbenzoxazole; 2,2'-hydroxy-5-methylphenylbenzotriazole; 2-(2'-hydroxy-5'-t-octylphenyl) benzotriazole; 2-(2'-hydroxy-5'-methylphenyl) benzotriazole; dibenzalazine; dianisoylmethane; 4-methoxy-4'-t-butyldibenzoylmethane; and 5-(3,3-dimethyl-2-norbornylidene)-3-pentan-2-one.

Examples of ultraviolet scattering agents include titanium dioxide, zinc oxide, and cerium oxide.

Among the above-described ultraviolet absorbents, sugar-derived ultraviolet absorbents are preferable, since the absorbers are water-soluble, as is the aforementioned xyloglucan.

When any of the sugar-derived ultraviolet absorbents is incorporated into the external-use composition of the first mode of the present invention, synergism of the sugar moiety of the absorber and the aforementioned xyloglucan increases the viscosity of the composition and forms a gel. When any of the aforementioned ultraviolet scattering agents is further incorporated into the composition, the viscosity of the composition increases to stably disperse the agent, and the composition may be improved in terms of retention of ultraviolet shielding effect. Therefore, the sugar-derived ultraviolet absorbents are preferably incorporated into the external-use composition of the first mode of the present invention.

In the external-use composition of the first mode of the present invention, the ratio of a ultraviolet absorbent to xyloglucan may be appropriately adjusted in accordance with the specific type of chosen ultraviolet absorbent and the form of the composition, and falls within a range of 2000:1–1:2 by weight. When the ultraviolet absorbents are incorporated in an amount in excess of the given range, substantial difficulty is encountered in obtaining the intended effect of improving the sensation provided by the composition containing the absorbers. When xyloglucan is incorporated in an amount in excess of the given range, xyloglucan may form polymer film in the composition, which may impair the sensation provided by the composition.

In the external-use composition of the first mode of the present invention, the ratio of the ultraviolet absorbent to xyloglucan is preferably 200:1–1:1 by weight.

In the external-use composition of the first mode of the present invention, the incorporation ratio of the ultraviolet scattering agent to xyloglucan may be appropriately adjusted in accordance with the specific type of chosen ultraviolet scattering agent and the form of the external-use composition, and falls within the range of 800:1–1:2 by weight. When the ultraviolet scattering agent is incorporated in an amount in excess of the given range, the agent may coagulate and substantial difficulty may be encountered in obtaining the intended effect of attaining stable dispersion of the agent in the composition. When xyloglucan is incorporated in an amount in excess of the given range, xyloglucan may form polymer film, which may impair the sensation provided by the composition.

In the external-use composition of the first mode of the present invention, the ratio of ultraviolet scattering agent to xyloglucan is preferably 200:1–1:1 by weight.

Thus, when the external-use composition contains both xyloglucan and ultraviolet shielding agents (ultraviolet absorbents and ultraviolet scattering agents), the composition may not have a sticky sensation caused by ultraviolet absorbents. When sugar-derived ultraviolet absorbents are incorporated, the viscosity of the external use-composition may increase to form a gel and ultraviolet scattering agents may be stably dispersed in the composition, to thereby maintain the effect of ultraviolet shielding agents with passage of time.

In the external-use composition of the first mode of the present invention, in addition to the aforementioned xyloglucan and ultraviolet shielding agents, other ingredients which are usually utilized in external-use compositions may be incorporated in accordance with needs, so long as they do not impair the intended effect of the present invention. (One or more additional ingredients may be incorporated in the composition.)

The following ingredients may be appropriately incorporated into the external-use composition of the first mode of the present invention: hydrocarbons, fats and oils, waxes, surfactants, silicones, higher alcohols, higher fatty acids, humectants, lower alcohols, antioxidants, antibacterial agents, neutralizing agents, pigments, perfumes, and purified water.

The following drugs may be appropriately incorporated into the external-use composition of the first mode of the present invention: amino acids, organic acids, vitamins, nicotinic acid amides, benzyl nicotinate, γ-oryzanol, allantoin, glycyrrhizic acid (salts), glycyrrhetinic acid and derivatives thereof, extracts from a variety of animals and plants, hinokitiol, bisabolol, eucalyptus, thymol, inositol, saponins, pantothenyl ethyl ether, ethynylestradiol, tranexamic acid, arbutin, cepharanthine, and placenta extract.

Ingredients which do not impair the sensation provided by the external-use composition of the first mode of the present invention are preferably incorporated thereinto. The possibility that xyloglucan may increase the viscosity of the composition in the presence of sugar should be considered.

B. A second mode of the present invention is directed to an external-use composition in which both xyloglucan and thickening polysaccharides are incorporated (hereinafter the composition will be referred to as the "external-use composition of the second mode of the present invention").

An external-use composition containing xyloglucan has a smooth sensation in use, rather than a sticky sensation provided when other polysaccharides are incorporated.

However, an external-use composition containing xyloglucan is not stable at high temperature; more specifically, viscosity may decrease with passage of time, and a sufficient effect may not be attained even if xyloglucan is incorporated into the composition.

The present inventors found that an external-use composition containing both xyloglucan and thickening polysaccharides has a smooth sensation which is provided when only xyloglucan is incorporated, and that the composition maintains its viscosity when allowed to stand at high temperature and is stable with passage of time. The inventors also found that the composition containing both xyloglucan and thickening polysaccharides is remarkably stable when it contains surfactants, particularly nonionic surfactants, more particularly sugar-derived nonionic surfactants.

In the external-use composition of the second mode of the present invention, thickening polysaccharides refer to all polysaccharides other than xyloglucan which are usually incorporated into an external use composition as a thickener, and xyloglucan is excluded from polysaccharides as defined in connection with the external-use composition of the second mode of the present invention.

In the external-use composition of the second mode of the present invention, xyloglucan is incorporated within the range of 0.01–10.0 wt. %, preferably 0.1–4.0 wt %, with respect to the entirety of the composition.

In the external-use composition of the second mode of the present invention, when xyloglucan is incorporated in an amount of less than 0.01 wt. % with respect to the entirety of the composition, substantial difficulty is encountered in obtaining the intended effect of improving the stability of the composition with passage of time at high temperature. When the amount thereof is in excess of 10.0 wt. % with respect to the entirety of the composition, xyloglucan forms polymer film in the composition, which may impair sensation in use of the composition.

In connection with the external-use composition of the second mode of the present invention, "thickening polysaccharides incorporated together with xyloglucan," refer to all polysaccharides which are usually incorporated into an external use composition as a thickener. Examples of thickening polysaccharides include, but are not limited to, cellulose, hydroxyethyl cellulose, hydroxypropyl cellulose, methylhydroxypropyl cellulose, methyl cellulose, carboxymethyl cellulose, quinsseed, carrageenan, pectin, mannan, curdlan, chondroitin sulfate, starch, galactan, dermatan sulfate, glycogen, acacia, heparan sulfate, hyaluronic acid, sodium hyaluronate, tragacanth gum, keratan sulfate, chondroitin, xanthan gum, mucoitin sulfate, hydroxyethyl guar gum, carboxymethyl guar gum, guar gum, dextran, kerato sulfate, locust bean gum, succinoglucane, charonin sulfate, chitin, chitosan, carboxymethyl chitin, mucopolysaccharides, and agar.

Among the above thickening polysaccharides, hydroxyethyl cellulose, xanthan gum, agar, locust bean gum, and tragacanth gum are preferably incorporated into the external-use composition of the second mode of the present invention, in view that they have high stability of viscosity particularly at high temperature.

One or more of the above thickening polysaccharides may be incorporated into the external-use composition of the second mode of the present invention.

In the external-use composition of the second mode of the present invention, the ratio of the xyloglucan to the thickening polysaccharides is 1:10–40:1 by weight, preferably 1:1–20:1.

When xyloglucan is incorporated in the external-use composition of the second mode of the present invention in an amount in excess of the given range, the viscosity of the composition may be unstable at high temperature. When thickening polysaccharides are incorporated into the composition in an amount in excess of the given range, the polysaccharides may impair sensation in use of the composition.

Thus, an excellent external-use composition which has a favorable sensation in use and is highly stable at high temperature is obtained by incorporating both xyloglucan and thickening polysaccharides into the composition. Surfactants may further be incorporated into the external-use composition of the second mode of the present invention so as to have a more excellent effect.

The following surfactants may be incorporated into the external-use composition of the second mode of the present invention without particular limitation:

Examples of anionic surfactants include fatty acid soap such as soap bar, sodium laurate, and sodium palmitate; higher alkyl sulfates such as sodium lauryl sulfate and potassium lauryl sulfate; alkyl ether sulfates such as triethanolamine polyoxyethylene laurylether sulfate (hereinafter polyoxyethylene will be referred to as POE), and sodium POE laurylether sulfate; N-acylsarcosinates such as sodium lauroylsarcosinate; higher fatty acid amide sulfonates such as sodium N-myristoyl N-methyl taurate, sodium cocoyl methyl taurate, and sodium lauryl methyl taurate; phosphates such as sodium POE oleylether phosphate and POE stearylether phosphate; sulfosuccinates such as di-2-ethylhexyl sodium sulfosuccinate, sodium monolauroyl monoethanolamide polyoxyethylene sulfosuccinate, and sodium lauryl polypropylene glycol sulfosuccinate; alkylbenzenesulfonates such as sodium linear dodecylbenzene sulfonate, triethanolamine linear dodecylbenzene sulfonate, and linear dodecylbenzenesulfonic acid; N-acylglutamates such as monosodium N-lauroyl glutamate, disodium N-stearoyl glutamate, and monosodium N-myristoyl-L-glutamate; higher fatty acid ester sulfates such as sodium hydrogenated glyceryl cocoate sulfate; sulfated oils such as Turkey red oil; POE alkyl ether carboxylates; POE alkylallyl ether carboxylate; α-olefin sulfonates; higher fatty acid ester sulfonates; secondary alcohol sulfates; higher fatty acid alkylolamide sulfates; sodium lauroyl monoethanolamide succinate; di-triethanolamine N-palmitoylaspartate; and sodium caseinate.

Examples of cationic surfactants include alkyltrimethylammonium salts such as stearyltrimethylammonium chloride and lauryltrimethylammonium chloride; dialkyldimethylammonium salts such as distearyldimethylammonium chloride; alkylpyridinium salts such as poly(N,N'-dimethyl-3,5-methylenepiperidinium) chloride and cetylpyridinium chloride; alkyl quaternary ammonium salts; alkyldimethylbenzylammonium salts; alkylisoquinolinium salts; dialkylmorpholinium salts; POE alkylamines; alkylamine salts; polyamine fatty acid derivatives; amyl alcohol fatty acid derivatives; benzalkonium chloride; and benzethonium chloride.

Examples of amphoteric surfactants include imidazoline amphoteric surfactants such as sodium 2-undecyl-N,N,N-(hydroxyethylcarboxymethyl)-2-imidazoline and a 2-cocoyl-2-imidazoliniumhydroxide-1-carboxyethyloxy 2 sodium salt; and betaine amphoteric surfactants such as 2-heptadecyl-N-carboxymethyl-N-hydroxyethylimidazolinium betaine, lauryldimethylaminoacetic acid betaine, alkylbetaine, amidobetaine, and sulfobetaine.

Examples of oleophilic nonionic surfactants include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerolsorbitan penta-2-ethylhexylate, and diglycerolsorbitan tetra-2-ethylhexylate; mono- or polyglycerides such as cotton seed oil fatty acid monoglyceride, glyceryl monoerucate, glyceryl sesquioleate, glyceryl monostearate, glyceryl α,α'-oleate pyroglutamate, and glyceryl monostearate malate; propylene glycol fatty acid esters such as propylene glycol monostearate; hydrogenated castor oil derivatives; and glycerin alkylethers.

Examples of hydrophilic nonionic surfactants include POE sorbitan fatty acid esters such as POE sorbitan monooleate, POE sorbitan monostearate, POE sorbitan monoolate, and POE sorbitan tetraoleate; POE sorbitol fatty acid esters such as POE sorbitol monolaurate, POE sorbitol monooleate, POE sorbitol pentaoleate, and POE sorbitol monostearate; POE glycerin fatty acid esters such as POE glycerin monostearate, POE glycerin monoisostearate, and POE glycerin triisostearate; POE fatty acid esters such as POE monooleate, POE distearates, POE monodioleates, and POE ethylene glycol distearates; POE alkyl ethers such as POE lauryl ether, POE oleyl ether, POE stearyl ether, POE behenyl ether, POE 2-octyldodecyl ether, and POE cholestanol ether; POE alkylphenyl ethers such as POE octylphenyl ether, POE nonylphenyl ether, and POE dinonylphenyl ether; pluaronic such as Pluronic®; POE-.polyoxypropylene (hereinafter polyoxypropylene will be referred to as POP) alkyl ethers such as POE.POP cetyl ether, POE.POP 2-decyltetradecyl ether, POE.POP monobutyl ether, POE.POP hydrogenated lanolin, and POE.POP glycerin ether; tetra POE.tetra POP ethylenediamine condensation products such as Tetronic®; POE castor oil or POE hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamate monoisostearate, and POE hydrogenated castor oil maleate; POE beeswax.lanolin derivatives such as POE sorbitol beeswax; alkanol amides such as coconut oil fatty acid diethanolamide, lauric acid monoethanolamide, and fatty acid isopropanolamide; POE propylene glycol fatty acid esters; POE alkylamines; POE fatty acid amides; sucrose fatty acid esters; POE nonylphenyl formaldehyde condensation products; alkylethoxydimethylamine oxides; and trioleyl phosphate.

Among these surfactants, nonionic surfactants are preferably incorporated into the external-use composition of the second mode of the present invention; more preferably sugar-derived nonionic surfactants such as POE sorbitan fatty acid esters, POE sorbitol fatty acid esters, or sucrose fatty acid esters.

When these sugar-derived nonionic surfactants are incorporated into the external-use composition of the second mode of the present invention, sugar moieties of the surfactant may interact with xyloglucan. Interaction may increase the viscosity of the composition or may cause the composition to gel, thereby improving the stability of the composition with passage of time.

One or more of these surfactants may be incorporated into the external-use composition of the second mode of the present invention.

In the external-use composition of the second mode of the present invention, the incorporation ratio of xyloglucan to the surfactants is 1:200–100:1 by weight, preferably 1:20–40:1.

When xyloglucan is incorporated into the external-use composition of the second mode of the present invention in an amount in excess of the given range, the viscosity of the composition may become unstable at high temperature. When surfactants are incorporated into the composition in an amount in excess of the given range, the surfactants may impair sensation in use of the composition.

When the surfactants are incorporated into the external-use composition along with xyloglucan and thickening polysaccharides, a more remarkable effect may be obtained as compared with the case where the surfactants are not incorporated.

In addition to the aforementioned ingredients (xyloglucan, thickening polysaccharides, and surfactants), other ingredients which are usually utilized for external-use compositions may be appropriately incorporated into the external-use composition of the second mode of the present invention, so long as they do not impair the intended effect of the present invention. (One or more of other ingredients may be incorporated into the composition.)

The following ingredients may be appropriately incorporated into the external-use composition of the second mode of the present invention: hydrocarbons, fats and oils, waxes, silicones, higher alcohols, higher fatty acids, humectants (other than thickening polysaccharides), lower alcohols, antioxidants, ultraviolet shielding agents, antibacterial agents, neutralizing agents, colorants, perfumes, and purified water.

The following drugs may be incorporated into the external-use composition of the second mode of the present invention: amino acids, organic acids, vitamins, nicotinic acid amides, benzyl nicotinate, γ-oryzanol, allantoin, glycyrrhizic acid (salts), glycyrrhetinic acid and derivatives thereof, extracts from a variety of animals and plants, hinokitiol, bisabolol, eucalyptus, thymol, inositol, saponins, pantothenyl ethyl ether, ethynylestradiol, tranexamic acid, arbutin, cepharanthine, and placenta extract.

C. A third mode of the present invention is directed to an external-use composition in which xyloglucan, thickening polysaccharides, and sericin are incorporated (hereinafter the composition will be referred to as the "external-use composition of the third mode of the present invention").

A variety of external-use compositions such as cosmetics are primarily designed to help human skin function normally.

In order to help a function of human skin, the external-use compositions are required to constantly keep the skin moist.

Therefore, in order to satisfy this requirement, there are provided a variety of external-use compositions in which water, humectants, and oils are appropriately incorporated.

Substances which participate in imparting moistness have been studied extensively, and a variety of humectants have been provided. Among humectants, water-soluble polyhydric alcohols are widely used as humectant ingredients in external-use compositions and drugs, since the alcohols are excellent in terms of moisturizing property or moisture absorbing property.

However, water-soluble polyhydric alcohols may have a sticky sensation in use, and may impair a sensation in use of an external use composition into which they are incorporated, although they have excellent effects of keeping human skin healthy and returning rough skin to normal condition.

Stickiness of an external use composition, which is caused by the incorporation of the water-soluble polyhydric alcohol, may be a serious problem, since the composition is required to have a favorable sensation in use.

The present inventors found that the aforementioned external-use composition containing xyloglucan, thickening polysaccharides, and sericin has not only good moisturizing effect on the skin but also favorable sensation in use, such as good fit for the skin, no stickiness, and smoothness, as does the external-use composition containing the water-soluble polyhydric alcohol.

In the external-use composition of the third mode of the present invention, the amount of incorporated xyloglucan is 0.01–5.0 wt. %, preferably 0.1–3.0 wt. %, with respect to the entirety of the composition.

In the external-use composition of the third mode of the present invention, when the amount of the incorporated xyloglucan is less than 0.01 wt. % with respect to the entirety of the composition, substantial difficulty is encountered in obtaining a moisturizing effect and a smooth sensation in use. When the amount thereof is in excess of 5.0 wt. % with respect to the entirety of the composition, xyloglucan forms polymer film in the composition, which may impair sensation in use of the composition.

Among thickening polysaccharides which are usually incorporated into external-use compositions, all thickening polysaccharides other than xyloglucan may be incorporated into the external-use composition of the third mode of the present invention, in the same manner as described in the section describing the second mode. Among the aforementioned thickening polysaccharides, hydroxyethyl cellulose and xanthan gum are preferably used, since the external-use composition of the third mode of the present invention containing these is excellent in that the composition spreads well on and has good fit for the skin.

The amount of incorporation of the above thickening polysaccharides is 0.01–5.0 wt. %, preferably 0.01–3.0 wt. %, with respect to the entirety of the external-use composition of the third mode of the present invention.

When the amount of incorporation is less than 0.01 wt. % with respect to the entirety of the composition, substantial difficulty is encountered in obtaining the intended effect of the composition in use, such as improved spreading on or good fit for the skin. When the amount thereof is in excess of 5.0 wt. % with respect to the entirety of the composition, thickening polysaccharides form a film on the skin, which causes a sticky sensation.

One or more of the thickening polysaccharides may be incorporated into the external-use composition of the third mode of the present invention.

In the external-use composition of the third mode of the present invention, the incorporation ratio of the xyloglucan to the thickening polysaccharides is 1:10–40:1, preferably 1:1–20:1 by weight.

When xyloglucan is incorporated into the external-use composition of the third mode of the invention in an amount in excess of the given range, the viscosity of the composition may be unstable at high temperature. When the thickening polysaccharides are incorporated into the composition in an amount in excess of the given range, the thickening polysaccharides may impair a favorable sensation in use of the composition.

Sericin which may be incorporated into the composition is a hydrophilic protein contained in silk threads which are produced by a silk gland when a silkworm forms a cocoon, and is rich in serine, aspartic acid, glutamic acid, glycine, and alanine.

As a commercial product, SERICINE (product of Pentafirm Co., Ltd., Switzerland) is available.

In the external-use composition of the third mode of the present invention, the amount of incorporated sericin is 0.001–5.0 wt. %, preferably 0.01–3.0 wt. %, with respect to the entirety of the composition.

In the external-use composition of the third mode of the present invention, when sericin is incorporated in an amount of less than 0.001 wt. % with respect to the entirety of the composition, substantial difficulty is encountered in improving a moisturizing effect of the composition and in providing favorable sensation in use such as good fit for the skin and no stickiness. When the amount thereof is more than 5.0 wt. % with respect to the entirety of the composition, sericin forms a film on the skin and provides a sticky sensation.

Thus, there may be provided the external-use composition of the third mode of the present invention, which has good moisturizing effect and a favorable sensation in use, such as good fit for the skin, no stickiness, and smoothness.

In addition to the aforementioned ingredients (xyloglucan, thickening polysaccharides, sericin), other ingredients which are usually utilized for external-use compositions may be appropriately incorporated into the external-use composition of the third mode of the present invention, so long as they do not impair the intended effect of the present invention. (One or more of other ingredients may be incorporated into the composition.)

The following ingredients may be appropriately incorporated into the external-use composition of the third mode of the present invention: hydrocarbons, fats and oils, waxes, silicones, surfactants, higher alcohols, higher fatty acids, humectants (other than thickening polysaccharides), lower alcohols, antioxidants, ultraviolet shielding agents, antibacterial agents, neutralizing agents, pigments, perfumes, and purified water.

The following drugs may be appropriately incorporated into the external-use composition of the third mode of the present invention: amino acids, organic acids, vitamins, nicotinic acid amides, benzyl nicotinate, γ-oryzanol, allantoin, glycyrrhizic acid (salts), glycyrrhetinic acid and derivatives thereof, extracts from a variety of animals and plants (other than sericin), hinokitiol, bisabolol, eucalyptus, thymol, inositol, saponins, pantothenyl ethyl ether, ethynylestradiol, tranexamic acid, arbutin, cepharanthine, and placenta extract.

D. A fourth mode of the present invention is directed to an external-use composition in which xyloglucan and carboxyvinylpolymers are incorporated (hereinafter the composition will be referred to as the "external-use composition of the fourth mode of the present invention").

Stability and sensation in use are often important properties in evaluation of an external-use composition, and to the extent possible an external-use composition should be excellent in these properties.

When surfactants are incorporated into an external-use composition in a large amount, the composition may have improved stability, but may have a poor sensation in use.

In order to maintain a favorable sensation in use, increase the viscosity, and improve the stability of an external-use composition, water-soluble polymers such as carboxyvinylpolymer have conventionally been incorporated into the composition.

However, carboxyvinylpolymers generally have poor salt tolerance, and when the polymers are incorporated into an external-use composition containing salts, the composition may have poor stability with passage of time, although the composition containing the polymers may have a favorable sensation in use.

The present inventors found that the external-use composition containing xyloglucan and carboxyvinylpolymers has excellent salt tolerance and stability with passage of time, and that the composition has a highly improved sensation in use as compared with a composition containing only carboxyvinylpolymers, to thereby complete the present invention.

In the external-use composition of the fourth mode of the present invention, the amount of incorporated xyloglucan is 0.05–10.0 wt. %, preferably 0.1–4.0 wt. %, with respect to the entirety of the composition.

When xyloglucan is incorporated into the external-use composition of the fourth mode of the present invention in an amount of less than 0.05 wt. % with respect to the entirety of the composition, substantial difficulty is encountered in obtaining the intended effect of improving the salt tolerance and sensation in use of the composition containing carboxyvinylpolymers. When the amount thereof is in excess of 10.0 wt. % with respect to the entirety of the composition, xyloglucan may form polymer film in the composition, which impairs a favorable sensation in use of the composition.

In the external-use composition of the fourth mode of the present invention, carboxyvinylpolymers incorporated together with xyloglucan are acidic polymers predominantly comprising acrylic acid polymers, and they are commercially available.

More specifically, examples of commercially available carboxyvinylpolymers include HIGHVIS WAKO 103, 104, and 105 (products of Wako Pure Chemical Industries, Ltd); CARBOPOL Series (product of BF Goodrich Co., Ltd); AQUPEC Series (product of Sumitomo Seika Chemicals Co., Ltd); and JUNLON PW Series (product of Nippon Pure Chemical Co., Ltd).

Salts of carboxyvinylpolymers may be incorporated into the external-use composition of the fourth mode of the present invention, and these carboxyvinylpolymer salts are encompassed by the concept of "carboxyvinylpolymers." For example, UNISAFE ECT-203 (carboxyvinylpolymer calcium.potassium salt; product of Nippon Oil and Fats Co., Ltd.), which is commercially available, may be incorporated into the composition.

In the external-use composition of the fourth mode of the present invention, the incorporation ratio of the xyloglucan to the carboxyvinylpolymers is 1:10–40:1 by weight. When carboxyvinylpolymers are incorporated into the external-use composition of the fourth mode of the present invention in an amount in excess of the given range, substantial difficulty is encountered in obtaining the intended effect of improving the salt tolerance and sensation in use of the composition containing the polymers. When xyloglucan is incorporated in an amount in excess of the given range, xyloglucan may form polymer film in the composition, and a favorable sensation in use of the composition may be reduced.

In the external-use composition of the fourth mode of the present invention, the incorporation ratio of xyloglucan to the carboxyvinylpolymers is preferably 1:2–10:1 by weight.

Thus, the external-use composition containing both xyloglucan and carboxyvinylpolymers may have improved salt tolerance and stability with passage of time and may have a highly improved sensation in use, as compared with an external-use composition containing only carboxyvinylpolymers.

Japanese Patent Application Laid-Open (kokai) No. 70264/1997 discloses an external-use composition which contains a complex of xyloglucan and a specific β-glucan. The external-use composition containing the complex may have "a sensation like that caused by coating with film" in use, since the complex, which complex is produced in order to effectively increase the viscosity of xyloglucan, is incorporated into the composition. In order to eliminate the above sensation of the composition containing the complex, a large amount of carboxyvinylpolymers, which polymers are incorporated in the external-use composition of the fourth mode of the present invention, must be incorporated into the above composition, since the viscosity of the complex is very high. However, a large amount of the polymers may cause the external-use composition to have poor salt tolerance.

The external-use composition of the fourth mode of the present invention, which contains xyloglucan and carboxyvinylpolymers, has an excellent sensation in use and excellent salt tolerance, and the composition which does not contain the complex is not required to contain a large amount of the polymers.

In addition to the aforementioned ingredients (xyloglucan, carboxyvinylpolymers), other ingredients which are usually utilized for external-use compositions may be appropriately incorporated into the external-use composition of the fourth mode of the present invention, so long as they do not impair the intended effect of the present invention. (One or more of other ingredients may be incorporated into the composition.)

The following ingredients may be appropriately incorporated into the external-use composition of the fourth mode of the present invention: hydrocarbons, fats and oils, waxes, silicones, surfactants, higher alcohols, higher fatty acids, humectants, lower alcohols, antioxidants, ultraviolet shielding agents, antibacterial agents, neutralizing agents, colorants, perfumes, and purified water.

The following drugs may be incorporated into the external-use composition of the fourth mode of the present invention: amino acids, organic acids, vitamins, nicotinic acid amides, benzyl nicotinate, γ-oryzanol, allantoin, glycyrrhizic acid (salts), glycyrrhetinic acid and derivatives thereof, extracts from a variety of animals and plants, hinokitiol, bisabolol, eucalyptus, thymol, inositol, saponins, pantothenyl ethyl ether, ethynylestradiol, tranexamic acid, arbutin, cepharanthine, and placenta extract.

Care must be taken in incorporation of surfactants into the external-use composition of fourth mode of the present invention, so as not to impair the intended effect of the present mode.

E. A fifth mode of the present invention is directed to an external-use composition in which xyloglucan and alkyl-modified carboxyvinylpolymers are incorporated (hereinafter the composition will be referred to as the "external-use composition of the fifth mode of the present invention").

Many external-use compositions such as cosmetics are produced by a colloid chemical method, such as emulsification or solubilization by use of water and oil components in order to provide adequate moisture for human skin, and many surfactants have conventionally been utilized in external-use compositions so as to produce stable external-use compositions.

Recently, however, external-use compositions have been required to contain only a limited amount of surfactants, in consideration of safety and environmental pollution.

Therefore, there has been developed a technique of providing a stable external-use composition in which alkyl-modified carboxyvinylpolymers are incorporated in place of generally-known surfactants such that the polymers are used as a means of emulsification or solubilization.

However, an external-use composition containing alkyl-modified carboxyvinylpolymers has an unfavorable sensation in use of poor fit for the skin and poor salt tolerance, and alkyl-modified carboxyvinylpolymers is inadequate for emulsification or solubilization in an external-use composition containing salts.

The present inventors found that an external-use composition containing xyloglucan and alkyl-modified carboxyvinylpolymers has an excellent sensation in use and has high salt tolerance, and that the composition may attain a further improvement in sensation in use by incorporation of silicone derivatives.

Xyloglucan is incorporated into the external-use composition of the fifth mode of the present invention in an amount of 0.05–10.0 wt. %, preferably 0.1–4.0 wt. %, with respect to the entirety of the composition.

When xyloglucan is incorporated into the external-use composition of the fifth mode of the present invention in an amount of less than 0.05 wt. % with respect to the entirety of the composition, substantial difficulty is encountered in obtaining the intended effect of improving salt tolerance and sensation in use. When the amount thereof is in excess of than 10.0 wt. % with respect to the entirety of the composition, xyloglucan may form polymer film in the composition, which may impair a sensation in use of the composition.

In the external-use composition of the fifth mode of the present invention, alkyl-modified carboxyvinylpolymers incorporated together with xyloglucan predominantly comprise acrylic acid.alkylmethacrylate copolymers. Examples of alkyl-modified carboxyvinylpolymers which are commercially available include CARBOPOL 1342, PEMULEN TR-1, and PEMULEN TR-2 (products of B F Goodrich Co., Ltd.).

Alkyl-modified carboxyvinylpolymers are incorporated into the external-use composition of the fifth mode of the present invention in an amount of 0.01–10.0 wt. %, preferably 0.05–5.0 wt. %, with respect to the entirety of the composition.

When alkyl-modified carboxyvinylpolymers are incorporated into the external-use composition of the fifth mode of the present invention in an amount of less than 0.01 wt. % with respect to the entirety of the composition, difficulty is encountered in emulsified the composition. When the amount thereof is in excess of 10.0 wt. % with respect to the entirety of the composition, emulsification and stability in emulsification of the composition may not improve with increase in the amount thereof.

In the external-use composition of the fifth mode of the present invention, the incorporation ratio of xyloglucan to alkyl-modified carboxyvinylpolymers is approximately 1:20–40:1 by weight, and the ratio may be adjusted within the above range in accordance with the form of the composition. When the polymers are incorporated into the composition in an amount in excess of the given range, substantial difficulty is encountered in obtaining the intended effect of improving the composition in sensation in use and salt tolerance. When xyloglucan is incorporated into the composition in an amount in excess of the above range, xyloglucan may form polymer film in the composition, which may impair sensation in use.

In the external-use composition of the fifth mode of the present invention, the incorporation ratio of xyloglucan to alkyl-modified carboxyvinylpolymers is preferably 1:5–20:1 by weight.

Thus, the external use composition containing both xyloglucan and alkyl-modified carboxyvinylpolymers may improve in salt tolerance and sensation in use, although an external-use composition containing the polymers has a sensation of poor fit for the skin.

Japanese Patent Application Laid-Open (kokai) No. 70264/1997 discloses an external-use composition which contains a complex of xyloglucan and a specific β-glucan. The external-use composition containing the complex may have "a sensation like that caused by coating with a film" in use, since the complex, which complex is produced in order to effectively increase the viscosity of xyloglucan, is incorporated into the composition. In order to eliminate the above sensation of the composition containing the complex, a large amount of alkyl-modified carboxyvinylpolymers, which polymers are incorporated in the external-use composition of the fifth mode of the present invention, must be incorporated into the above composition, since the viscosity of the complex is very high. However, a large amount of the polymers may cause the external-use composition to have poor salt tolerance.

The external-use composition of the fifth mode of the present invention, which contains xyloglucan and alkyl-modified carboxyvinylpolymers, has an excellent sensation in use and excellent salt tolerance, and the composition which does not contain the complex is not required to be contain a large amount of the polymers.

In addition to the aforementioned xyloglucan and alkyl-modified carboxyvinylpolymers, silicone derivatives may be further incorporated into the external-use composition of the fifth mode of the present invention in order to further improve sensation in use.

Silicone derivatives which may be incorporated into the external-use composition of the fifth mode of the present invention are not particularly limited, and those which are routinely incorporated into external-use compositions may be broadly employed without limitation.

The following silicone derivatives may be incorporated into the external-use composition of the fifth mode of the present invention: polyether-modified silicones such as dimethylpolysiloxane, methylphenylpolysiloxane, highly-polymerized dimethylpolysiloxane, and dimethylsiloxane-methyl(polyoxyethylene)siloxane copolymers; cyclic silicones such as decamethylcyclopentasiloxane and octamethylcyclotetrasiloxane; and amino-modified silicone such as highly-polymerized dimethylsiloxane.methyl (aminopropyl)siloxane copolymers.

The above silicone derivatives may be incorporated into the external-use composition of the fifth mode of the present invention singly or in combination of two or more.

In the external-use composition of the fifth mode of the present invention, the amount of incorporated silicone derivatives is 0.01–10.0 wt. %, preferably 0.05–5.0 wt. %, with respect to the entirety of the composition.

When silicone derivatives are incorporated into the external-use composition of the fifth mode of the present invention in an amount of less than 0.01 wt. % with respect to the entirety of the composition, substantial difficulty is encountered in further improving sensation in use of the composition. When the amount thereof is in excess of 10.0 wt. % with respect to the entirety of the composition, the composition may have poor stability.

In the external-use composition of the fifth mode of the present invention, the incorporation ratio of xyloglucan to silicone derivatives is 1:10–20:1 by weight, and the ratio may be adjusted within the above range in accordance with the form of the composition. When the silicones are incorporated into the composition in an amount in excess of the given range, the composition may have poor stability. When xyloglucan is incorporated into the composition in an amount in excess of the given range, xyloglucan may form polymer film in the composition, which may impair sensation in use.

In the external-use composition of the fifth mode of the present invention, the incorporation ratio of xyloglucan to silicone derivatives is preferably 1:5–10:1 by weight.

Thus, in the external-use composition containing xyloglucan and alkyl-modified carboxyvinylpolymers, silicone derivatives may be further incorporated in order to further improve sensation in use of the composition.

In addition to the aforementioned ingredients (xyloglucan, alkyl-modified carboxyvinylpolymers, and silicone derivatives), other ingredients which are usually utilized for external-use compositions may be appropriately incorporated into the external-use composition of the fifth mode of the present invention, so long as they do not impair the intended effect of the present invention. (One or more of other ingredients may be incorporated into the composition.)

The following ingredients may be incorporated into the external-use composition of the fifth mode of the present invention: hydrocarbons, fats and oils, waxes, surfactants, higher alcohols, higher fatty acids, humectants, lower alcohols, antioxidants, ultraviolet shielding agents, antibacterial agents, neutralizing agents, colorants, perfumes, and purified water.

The following drugs may be incorporated into the external use composition of the fifth mode of the present invention: amino acids, organic acids, vitamins, nicotinic acid amides, benzyl nicotinate, γ-oryzanol, allantoin, glycyrrhizic acid (salts), glycyrrhetinic acid and derivatives thereof, extracts from a variety of animals and plants, hinokitiol, bisabolol, eucalyptus, thymol, inositol, saponins, pantothenyl ethyl ether, ethynylestradiol, tranexamic acid, arbutin, cepharanthine, and placenta extract.

Care must be taken in incorporation of surfactants into the external-use composition of fifth mode of the present invention, so as not to impair the intended effect.

The external-use compositions of the aforementioned modes of the present invention may take any form, and may be applied to a variety of external-use compositions, including aqueous solutions, solubilizations, emulsifications, powder-dispersions, water-oil two-layered systems, and water-oil-powder three-layered systems. The external-use compositions may be processed into products comprising a variety of cosmetics, including basic cosmetics such as lotions, milky lotions, creams, and packs; make-up cosmetics such as lipsticks and foundations; hair-care products such as shampoos, rinses, and hair-dyes; and specific-use cosmetics such as sunscreen products, drugs such as ointments, and quasi-drugs.

EXAMPLES

The present invention will next be described in more detail by way of examples, which should not be construed as limiting the invention thereto. In the examples, unless otherwise indicated, the amount of a component is described in terms of weight % with respect to the entirety of the composition.

A. Examples of a First Mode of the Present Invention

Prior to disclosure of formulation examples, the evaluation methods applied to the external-use composition of the present invention will first be described.

1. Sensory Analysis of Sensation in Use

Sensation in use of each test composition was judged by 60 panelists; 30 men and 30 women. Sensation in use was judged on the basis of the number of panelists who reported a sticky sensation. Evaluation standards are as follows.

Evaluation Standards

A: less than 5 panelists have reported a sticky sensation
B: at least 5 and less than 10 panelists have reported a sticky sensation
C: at least 10 and less than 30 panelists have reported a sticky sensation
D: 30 or more panelists have reported a sticky sensation 2. Evaluation of Viscosity Stability Each test composition was left at 50° C., and the viscosity stability with the passage of time was judged by measurement of viscosity (25° C.) immediately after preparation and 30 days after preparation, by use of a B-type viscometer.

3. Evaluation of Retention of Ultraviolet Shielding Effect

The in vitro SPF of each test composition was measured immediately after preparation and 30 days after preparation (stored at room temperature).

Specifically, two pieces of adhesive tape were overlaid in such a manner that the adhesive faces contact each other. A sample was applied thereto to a uniform thickness (2.0 mg/cm$^2$), and after 15 or more minutes, ultraviolet rays were radiated from a predetermined distance (10 mm). By use of a spectroradiometer, ultraviolet light that passed therethrough was detected in a range of 290 to 400 nm at intervals of 2 nm at 4 or more points on the tape.

In vitro SPF was calculated through multiplication of the detected value and a coefficient of effect.

In the following examples, "GLYROID 6C" of Dainippon Pharmaceutical Co., Ltd. was used as xyloglucan.

Example A1

Cream

|  | amount (wt. %) |
|---|---|
| (aqueous phase) | |
| (1) purified water | balance |
| (2) 1,3-butylene glycol | 5.0 |
| (3) xyloglucan | 2.0 |
| (oil phase) | |
| (4) octyl p-methoxycinnamate | 5.0 |
| (5) oxybenzone | 2.0 |
| (6) squalane | 10.0 |
| (7) vaseline | 5.0 |
| (8) stearyl alcohol | 3.0 |
| (9) stearic acid | 3.0 |
| (10) glyceryl monostearate | 3.0 |
| (11) poly(ethyl acrylate) | 1.0 |
| (12) antioxidant | suitable amount |
| (13) preservative | suitable amount |
| (14) perfume | suitable amount |

Example A2

Cream

|  | amount (wt. %) |
|---|---|
| (aqueous phase) | |
| (1) purified water | balance |
| (2) 1,3-butylene glycol | 5.0 |
| (3) xyloglucan | 2.0 |
| (4) 2-hydroxy-4-methoxybenzophenone-5-sulfonate | 5.0 |
| (oil phase) | |
| (5) oxybenzone | 2.0 |
| (6) squalane | 10.0 |
| (7) vaseline | 5.0 |
| (8) stearyl alcohol | 3.0 |
| (9) stearic acid | 3.0 |
| (10) glyceryl monostearate | 3.0 |
| (11) poly(ethyl acrylate) | 1.0 |
| (12) antioxidant | suitable amount |
| (13) preservative | suitable amount |
| (14) perfume | suitable amount |

Example A3

Cream

|  | amount (wt. %) |
|---|---|
| (aqueous phase) | |
| (1) purified water | balance |
| (2) 1,3-butylene glycol | 5.0 |
| (3) xyloglucan | 2.0 |
| (4) 2-hydroxy-4-(2-β-glucopyranosiloxy)propoxybenzophenone | 5.0 |
| (oil phase) | |
| (5) oxybenzone | 2.0 |
| (6) squalane | 10.0 |
| (7) vaseline | 5.0 |
| (8) stearyl alcohol | 3.0 |
| (9) stearic acid | 3.0 |
| (10) glyceryl monostearate | 3.0 |
| (11) poly(ethyl acrylate) | 1.0 |
| (12) antioxidant | suitable amount |
| (13) preservative | suitable amount |
| (14) perfume | suitable amount |

Example A4

Cream

|  | amount (wt. %) |
|---|---|
| (aqueous phase) | |
| (1) purified water | balance |
| (2) 1,3-butylene glycol | 5.0 |
| (3) xyloglucan | 2.0 |
| (4) 2-hydroxy-4-(2-β-glucopyranosiloxy)propoxybenzophenone | 5.0 |
| (5) titanium dioxide | 5.0 |
| (oil phase) | |
| (6) oxybenzone | 2.0 |
| (7) squalane | 10.0 |
| (8) vaseline | 5.0 |
| (9) stearyl alcohol | 3.0 |
| (10) stearic acid | 3.0 |

-continued

|  | amount (wt. %) |
|---|---|
| (11) glyceryl monostearate | 3.0 |
| (12) poly(ethyl acrylate) | 1.0 |
| (13) antioxidant | suitable amount |
| (14) preservative | suitable amount |
| (15) perfume | suitable amount |

Comparative Example A1

Cream

|  | amount (wt. %) |
|---|---|
| (aqueous phase) | |
| (1) purified water | balance |
| (2) 1,3-butylene glycol | 5.0 |
| (3) carboxyvinylpolymer | 0.1 |
| (4) triethanolamine | 1.0 |
| (5) octyl p-methoxycinnamate | 5.0 |
| (oil phase) | |
| (6) oxybenzone | 2.0 |
| (7) squalane | 10.0 |
| (8) vaseline | 5.0 |
| (9) stearyl alcohol | 3.0 |
| (10) stearic acid | 3.0 |
| (11) glyceryl monostearate | 3.0 |
| (12) poly(ethyl acrylate) | 1.0 |
| (13) antioxidant | suitable amount |
| (14) preservative | suitable amount |
| (15) perfume | suitable amount |

Comparative Example A2

Cream

|  | amount (wt. %) |
|---|---|
| (aqueous phase) | |
| (1) purified water | balance |
| (2) 1,3-butylene glycol | 5.0 |
| (3) 2-hydroxy-4-methoxybenzophenone-5-sulfonate | 5.0 |
| (4) carboxyvinylpolymer | 0.1 |
| (5) triethanolamine | 1.0 |
| (oil phase) | |
| (6) oxybenzone | 2.0 |
| (7) squalane | 10.0 |
| (8) vaseline | 5.0 |
| (9) stearyl alcohol | 3.0 |
| (10) stearic acid | 3.0 |
| (11) glyceryl monostearate | 3.0 |
| (12) poly(ethyl acrylate) | 1.0 |
| (13) antioxidant | suitable amount |
| (14) preservative | suitable amount |
| (15) perfume | suitable amount |

Comparative Example A3

Cream

|  | amount (wt. %) |
|---|---|
| (aqueous phase) | |
| (1) purified water | balance |
| (2) 1,3-butylene glycol | 5.0 |
| (3) 2-hydroxy-4-(2-β-glucopyranosiloxy) propoxybenzophenone | 5.0 |
| (4) carboxyvinylpolymer | 0.1 |
| (5) triethanolamine | 1.0 |
| (oil phase) | |
| (6) oxybenzone | 2.0 |
| (7) squalane | 10.0 |
| (8) vaseline | 5.0 |
| (9) stearyl alcohol | 3.0 |
| (10) stearic acid | 3.0 |
| (11) glyceryl monostearate | 3.0 |
| (12) poly(ethyl acrylate) | 1.0 |
| (13) antioxidant | suitable amount |
| (14) preservative | suitable amount |
| (15) perfume | suitable amount | comparative Example A4

Cream

|  | amount (wt. %) |
|---|---|
| (aqueous phase) | |
| (1) purified water | balance |
| (2) 1,3-butylene glycol | 5.0 |
| (3) 2-hydroxy-4-(2-β-glucopyranosiloxy) propoxybenzophenone | 5.0 |
| (4) titanium dioxide | 5.0 |
| (5) carboxyvinylpolymer | 0.1 |
| (6) triethanolamine | 1.0 |
| (oil phase) | |
| (7) oxybenzone | 2.0 |
| (8) squalane | 10.0 |
| (9) vaseline | 5.0 |
| (10) stearyl alcohol | 3.0 |
| (11) stearic acid | 3.0 |
| (12) glyceryl monostearate | 3.0 |
| (13) poly(ethyl acrylate) | 1.0 |
| (14) antioxidant | suitable amount |
| (15) preservative | suitable amount |
| (16) perfume | suitable amount |

<Method for Preparation>

In the above Examples A1 to A4 and Comparative Examples A1 to A4, the aqueous phase and the oil phase were heated to 70° C. for dissolution of the ingredients. Thereafter, the oil phase was added to the aqueous phase and the resultant mixture was emulsified by use of a homogenizer. The resultant emulsion was cooled by use of a heat exchanger to thereby obtain a cream.

Each cream of the examples and the comparative examples was subjected to sensory analysis of sensation in use, evaluation of viscosity stability, and evaluation of retention of ultraviolet shielding effect.

The results are described in the following Table A1 (sensory analysis of sensation in use), Table A2 (evaluation of viscosity stability), and Table A3 (evaluation of retention of ultraviolet shielding effect).

TABLE A1

| Item | Example A1 | Example A2 | Example A3 | Example A4 |
| --- | --- | --- | --- | --- |
| Sensation in use | B | B | A | A |

| Item | Comparative Example A1 | Comparative Example A2 | Comparative Example A3 | Comparative Example A4 |
| --- | --- | --- | --- | --- |
| Sensation in use | D | C | B | B |

The results in Table A1 show that external-use compositions of the first mode of the present invention, which contain xyloglucan and an ultraviolet absorbent, are superior in terms of sensation in use to the corresponding comparative compositions, which do not contain xyloglucan.

The examples and comparative examples also show that compositions which incorporate a sugar-derived ultraviolet absorbent exhibit improved sensation in use as compared with compositions which incorporate another-typed ultraviolet absorbents.

TABLE A2

| Item | Example A1 | Example A2 | Example A3 | Example A4 |
| --- | --- | --- | --- | --- |
| viscosity immediately after preparation | 2300 cps | 2200 cps | 3510 cps | 3450 cps |
| viscosity 30 days later | 2300 cps | 2150 cps | 3450 cps | 3450 cps |

| Item | Comparative Example A1 | Comparative Example A2 | Comparative Example A3 | Comparative Example A4 |
| --- | --- | --- | --- | --- |
| viscosity immediately after preparation | 2000 cps | 1900 cps | 2100 cps | 2200 cps |
| viscosity 30 days later | 1500 cps | 1600 cps | 1800 cps | 2000 cps |

The results in Table A2 show that the external-use compositions of the first mode of the present invention, which incorporate xyloglucan and an ultraviolet absorbent, are superior in terms of viscosity stability with the passage of time to the corresponding comparative compositions, which compositions do not incorporate xyloglucan.

Furthermore, the results definitely show that a composition which incorporates a sugar-derived ultraviolet absorbent and xyloglucan (Example A3 and Example A4) has improved viscosity stability as compared with other compositions.

TABLE A3

| Item | Example A1 | Example A2 | Example A3 | Example A4 |
| --- | --- | --- | --- | --- |
| Viscosity immediately after preparation | 12.1 | 11.3 | 11.5 | 14.3 |
| Viscosity 30 days later | 10.2 | 9.9 | 10.1 | 13.9 |

| Item | Comparative Example A1 | Comparative Example A2 | Comparative Example A3 | Comparative Example A4 |
| --- | --- | --- | --- | --- |
| Viscosity immediately after preparation | 11.5 | 11.0 | 10.9 | 13.8 |
| Viscosity 30 days later | 9.8 | 8.9 | 8.5 | 10.9 |

The results in Table A3 show that the external-use composition of the first mode of the present invention, which incorporates xyloglucan and an ultraviolet absorbent, is superior in terms of retention of the ultraviolet shielding effect to the corresponding test composition, which composition does not incorporate xyloglucan and is used in the corresponding comparative example.

This tendency is especially evident when a composition incorporates both a sugar-derived ultraviolet absorbent and an ultraviolet scattering agent (Example A4). This fact supports that the viscosity of a composition is increased by the presence of a sugar-derived ultraviolet absorbent, and thus the dispersion stability of the ultraviolet scattering agent is maintained with the passage of time (see the above Table A2).

A variety of product forms of the external-use compositions of the first mode of the present invention will be described in the following examples. The external-use compositions of the first mode of the present invention of these examples were tested through the above methods, and all external-use compositions of the first mode of the present invention were shown to be significantly superior to the xyloglucan-free compositions of comparative examples in terms of (1) sensation in use, (2) viscosity stability with the passage of time, and (3) retention of ultraviolet shielding effect.

Example A5

Lotion

| | amount (wt. %) |
| --- | --- |
| (1) purified water | balance |
| (2) dipropylene glycol | 5.0 |
| (3) xyloglucan | 0.1 |
| (4) 1,3-butylene glycol | 10.0 |
| (5) polyethylene glycol 400 | 10.0 |
| (6) ethyl alcohol | 16.0 |
| (7) POE (60) hydrogenated castor oil | 3.0 |
| (8) 2-hydroxy-4-methoxybenzophenone-5-sulfonate | 5.0 |
| (9) perfume | suitable amount |

<Method for Preparation>

The POE (60) hydrogenated castor oil and the perfume were dissolved in the ethyl alcohol (alcoholic phase). The remaining alcohol ingredients, the xyloglucan, and the 2-hydroxy-4-methoxybenzophenone-5-sulfonate were added to purified water and sufficiently dissolved (aqueous phase). The alcoholic phase was added to the aqueous phase, and the resultant mixture was sufficiently stirred to thereby obtain the desired lotion.

Example A6
Lipstick

| | amount (wt. %) |
|---|---|
| (1) titanium dioxide | 4.5 |
| (2) Red #201 (Lithol rubine B) | 0.5 |
| (3) Red #202 (Lithol rubine BCA) | 2.0 |
| (4) Red #223 (Tetrabromofluorescein) | 0.05 |
| (5) ceresin | 4.0 |
| (6) candelilla wax | 8.0 |
| (7) carnauba wax | 2.0 |
| (8) castor oil | 30.0 |
| (9) diglyceryl isostearate | 37.95 |
| (10) POE (25) POP (20) 2-tetradecyl ether | 1.0 |
| (11) purified water | balance |
| (12) glycerin | 2.0 |
| (13) xyloglucan | 0.5 |
| (14) propylene glycol | 1.0 |
| (15) 2-hydroxy-4-methoxybenzophenone | 2.0 |
| (16) antioxidant | suitable amount |
| (17) perfume | suitable amount |

<Method for Preparation>

The titanium dioxide, Red #201, and Red #202 were added to a portion of the castor oil and processed by a roller (pigment portion). The red #223 was dissolved in the remainder of the castor oil (dye portion). The purified water, glycerin, propylene glycol, and xyloglucan were homogeneously dissolved at 80° C. (aqueous phase). The remaining components were mixed and dissolved with heat. The pigment portion and the dye portion were added thereto and the resultant mixture was homogeneously dispersed by use of a homogenization mixer. Thereafter, the aqueous phase was added thereto and the resultant mixture was dispersed and emulsified by use of the homogenization mixer. The resultant emulsion was poured in a mold and cooled immediately to thereby obtain the desired lipstick.

Example A7
Powdery Foundation

| | amount (wt. %) |
|---|---|
| (1) talc | 20.3 |
| (2) mica | 33.0 |
| (3) kaolin | 5.0 |
| (4) titanium dioxide | 10.0 |
| (5) mica titanium | 1.0 |
| (6) zinc stearate | 1.0 |
| (7) xyloglucan | 2.0 |
| (8) yellow iron oxide | 3.0 |
| (9) black iron oxide | 0.2 |
| (10) nylon powder | 10.0 |
| (11) squalane | 6.0 |
| (12) lanolin acetate | 1.0 |
| (13) octyldodecyl myristate | 2.0 |
| (14) neopentyl glycol diisooctanoate | 2.0 |
| (15) sorbitan monooleate | 0.5 |
| (16) isopropyl p-methoxycinnamate | 2.0 |
| (17) antioxidant | suitable amount |
| (18) perfume | suitable amount |

<Method for Preparation>

The talc, yellow iron oxide, and black iron oxide were mixed by use of a blender. The remaining powdery components were added thereto and sufficiently mixed, followed by addition of the binder and preservation. After the color was adjusted, the perfume was sprayed onto the mixture and homogeneously mixed. Thereafter, the mixture was pulverized in a mill, passed through a sieve, and compression-mold on a dish to thereby obtain the desired powdery foundation.

Example A8
Emulsion Foundation

| | amount (wt. %) |
|---|---|
| (powder portion) | |
| (1) talc | 3.0 |
| (2) titanium dioxide | 5.0 |
| (3) red iron oxide | 0.5 |
| (4) yellow iron oxide | 1.4 |
| (5) black iron oxide | 0.1 |
| (aqueous phase) | |
| (6) polyoxyethylene sorbitan monostearate | 0.9 |
| (7) triethanolamine | 1.0 |
| (8) propylene glycol | 5.0 |
| (9) purified water | 46.4 |
| (10) xyloglucan | 1.0 |
| (11) 2-hydroxy-4-(2-β-glucopyranosiloxy) propoxybenzophenone | 10.0 |
| (Oil phase) | |
| (12) stearic acid | 2.2 |
| (13) isohexadecyl alcohol | 7.0 |
| (14) glycerin monostearate | 2.0 |
| (15) liquid lanolin | 2.0 |
| (16) liquid paraffin | 8.0 |
| (17) preservative | suitable amount |
| (18) perfume | suitable amount |

<Method for Preparation>

The xyloglucan was dispersed in the propylene glycol, and the mixture was added to the purified water. The resultant solution was stirred at 70° C. by use of a homogenization mixer, and the remaining components of the aqueous phase were added thereto and stirred sufficiently (aqueous phase). The components of the powder portion were mixed and crushed sufficiently, and added to the aqueous phase with stirring. The resultant mixture was mixed at 70° C. by use of a homogenization mixer. The components of the oil phase were dissolved with heat at 70° C. to 80° C., and the resultant oil phase was added to the mixture. The resultant mixture was mixed by use of the homogenization mixer at 70° C. Thereafter, the mixture was cooled with stirring, and the perfume was added thereto at 45° C. The resultant mixture was cooled to room temperature. Finally, the mixture was degassed and filled in a container to thereby obtain the desired emulsified foundation.

B. Examples of a Second Mode of the Present Invention

Prior to disclosure of formulation examples, evaluation methods applied to the external-use composition of the present invention are first described.

1. Sensory Analysis of Sensation in Use

Sensation in use of each test composition was judged by 60 panelists; 30 men and 30 women. Sensation in use was judged on the basis of the number of panelists who reported a sticky sensation. Evaluation standards are as follows.

Evaluation Standards

A: less than 5 panelists have reported a sticky sensation
B: at least 5 and less than 10 panelists have reported a sticky sensation
C: at least 10 and less than 30 panelists reported a sticky sensation
D: 30 or more panelists have reported a sticky sensation 2. Evaluation of Viscosity Stability Each test composition was left at 50° C., and the viscosity stability with the passage of time was judged by measurement of viscosity (25° C.) immediately after preparation and 30 days after preparation, by use of a B-type viscometer.

In the following examples, "GLYROID 6C" of Dainippon Pharmaceutical Co., Ltd. was used as xyloglucan.

Lotions whose formulas were described in the following Examples B1 to B5 and Comparative Example B1 were prepared through conventional methods, and these test compositions were evaluated by sensory analysis of sensation in use and evaluation of viscosity stability.

The results were described in the following Table B1.

Example B1
Lotion

|  | amount (wt. %) |
|---|---|
| (oil phase) | |
| (1) cetyl alcohol | 1.0 |
| (2) beeswax | 0.5 |
| (3) vaseline | 2.0 |
| (4) squalane | 6.0 |
| (5) dimethylpolysiloxane | 2.0 |
| (aqueous phase) | |
| (6) glycerin | 4.0 |
| (7) 1,3-butylene glycol | 4.0 |
| (8) POE (20) oleyl alcohol ether | 0.5 |
| (9) xyloglucan | 2.0 |
| (10) locust bean gum | 0.1 |
| (11) preservative | suitable amount |
| (12) colorant | suitable amount |
| (13) perfume | suitable amount |
| (14) purified water | balance |

Example B2

|  | amount (wt. %) |
|---|---|
| (oil phase) | |
| (1) cetyl alcohol | 1.0 |
| (2) beeswax | 0.5 |
| (3) vaseline | 2.0 |
| (4) squalane | 6.0 |
| (5) dimethylpolysiloxane | 2.0 |
| (aqueous phase) | |
| (6) glycerin | 4.0 |
| (7) 1,3-butylene glycol | 4.0 |
| (8) POE (20) oleyl alcohol ether | 0.5 |
| (9) xyloglucan | 2.0 |
| (10) locust bean gum | 0.5 |
| (11) preservative | suitable amount |
| (12) colorant | suitable amount |
| (13) perfume | suitable amount |
| (14) purified water | balance |

Example B3
Lotion

|  | amount (wt. %) |
|---|---|
| (oil phase) | |
| (1) cetyl alcohol | 1.0 |
| (2) beeswax | 0.5 |
| (3) vaseline | 2.0 |
| (4) squalane | 6.0 |
| (5) dimethylpolysiloxane | 2.0 |
| (aqueous phase) | |
| (6) glycerin | 4.0 |
| (7) 1,3-butylene glycol | 4.0 |
| (8) sucrose fatty acid ester | 0.5 |
| (9) xyloglucan | 2.0 |
| (10) locust bean gum | 0.5 |
| (11) preservative | suitable amount |
| (12) colorant | suitable amount |
| (13) perfume | suitable amount |
| (14) purified water | balance |

Example B4
Lotion

|  | amount (wt. %) |
|---|---|
| (oil phase) | |
| (1) cetyl alcohol | 1.0 |
| (2) beeswax | 0.5 |
| (3) vaseline | 2.0 |
| (4) squalane | 6.0 |
| (5) dimethylpolysiloxane | 2.0 |
| (aqueous phase) | |
| (6) glycerin | 4.0 |
| (7) 1,3-butylene glycol | 4.0 |
| (8) acrylic acid.alkylmethacrylate copolymer | 1.0 |
| (9) xyloglucan | 2.0 |
| (10) locust bean gum | 0.1 |
| (11) preservative | suitable amount |
| (12) colorant | suitable amount |
| (13) perfume | suitable amount |
| (14) purified water | balance |

Example B5
Lotion

|  | amount (wt. %) |
|---|---|
| (oil phase) | |
| (1) cetyl alcohol | 1.0 |
| (2) beeswax | 0.5 |
| (3) vaseline | 2.0 |
| (4) squalane | 6.0 |
| (5) dimethylpolysiloxane | 2.0 |
| (aqueous phase) | |
| (6) glycerin | 4.0 |
| (7) 1,3-butylene glycol | 4.0 |
| (8) acrylic acid.alkylmethacrylate copolymer | 1.0 |
| (9) xyloglucan | 2.0 |
| (10) locust bean gum | 0.5 |
| (11) preservative | suitable amount |
| (12) colorant | suitable amount |
| (13) perfume | suitable amount |
| (14) purified water | balance |

Comparative Example B1

Lotion

|  | amount (wt. %) |
|---|---|
| (oil phase) | |
| (1) cetyl alcohol | 1.0 |
| (2) beeswax | 0.5 |
| (3) vaseline | 2.0 |
| (4) squalane | 6.0 |
| (5) dimethylpolysiloxane | 2.0 |
| (aqueous phase) | |
| (6) glycerin | 4.0 |
| (7) 1,3-butylene glycol | 4.0 |
| (8) acrylic acid.alkylmethacrylate copolymer | 1.0 |
| (9) xyloglucan | 2.0 |
| (10) preservative | suitable amount |
| (11) colorant | suitable amount |
| (12) perfume | suitable amount |
| (13) purified water | balance |

TABLE B1

|  | sensation in use | Immediately after preparation | 30 days later |
|---|---|---|---|
|  |  | viscosity (cps) | |
| Example B1 | A | 25000 | 23600 |
| Example B2 | A | 92300 | 91200 |
| Example B3 | A | 113000 | 109000 |
| Example B4 | B | 20800 | 17900 |
| Example B5 | A | 84600 | 68000 |
| Comparative Example B1 | C | 2100 | 510 |

The results in Table B1 confirm that an external-use composition in which xyloglucan and a thickening polysaccharide are incorporated is superior in terms of both sensation in use and viscosity stability with the passage of time. Also, comparison of Examples B1, B2 (containing POE (20) oleyl alcohol ether as a surfactant) and Examples B4, B5 (containing an acrylic acid-alkylmethacrylate copolymer instead of POE (20) oleyl alcohol ether) show that if a surfactant is incorporated in a composition, the viscosity stability with passage of time under high temperature is further improved. Furthermore, as understood from Example B3, it was found that the viscosity stability is still further improved by the incorporation of sugar-derived surfactants.

A variety of product forms of the external-use compositions of a second mode of the present invention were described in the following examples. Each external-use composition of the second mode of the present invention was ranked "A" among the above standards in terms of sensation in use. Also, with regard to the viscosity stability with passage of time at high temperature, each composition of the second mode of the present invention was significantly superior to the composition of the corresponding comparative example in which water was used instead of a thickening polysaccharide.

Example B6

Cream

|  | amount (wt. %) |
|---|---|
| (1) cetyl alcohol | 5.0 |
| (2) stearic acid | 3.0 |
| (3) vaseline | 5.0 |
| (4) squalane | 10.0 |
| (5) glyceryl tri-2-ethylhexanoate | 7.0 |
| (6) dipropylene glycol | 5.0 |
| (7) glycerin | 5.0 |
| (8) propyleneglycol monostearate | 1.5 |
| (9) POE (20) cetyl alcohol ether | 1.5 |
| (10) triethanolamine | 1.0 |
| (11) xyloglucan | 1.0 |
| (12) hydroxyethylcellulose | 0.5 |
| (13) preservative | suitable amount |
| (14) antioxidant | suitable amount |
| (15) perfume | suitable amount |
| (16) purified water | balance |

<Method for Preparation>

The humectant and alkali were added to the purified water, and the temperature of the resultant solution was adjusted to 70° C. (aqueous phase). The oily components were dissolved with heat. The surfactant, the preservative, the antioxidant, and the perfume were added thereto and the temperature of the resultant mixture was adjusted to 70° C. The mixture was added to the aqueous phase and the resultant mixture was subjected to preliminary emulsification. The emulsified particles of the emulsion were homogenized by use of a homogenization mixer. Thereafter, the emulsion was degassed, filtered, and cooled to thereby obtain the desired cream.

Example B7

Milky Lotion

|  | amount (wt. %) |
|---|---|
| (1) cetyl alcohol | 1.0 |
| (2) beeswax | 0.5 |
| (3) vaseline | 2.0 |
| (4) squalane | 6.0 |
| (5) dimethylpolysiloxane | 2.0 |
| (6) ethanol | 5.0 |
| (7) glycerin | 4.0 |
| (8) 1,3-butylene glycol | 4.0 |
| (9) POE (10) monooleic acid ester | 1.0 |
| (10) glyceryl monostearate | 1.0 |
| (11) xyloglucan | 2.0 |
| (12) xanthan gum | 0.1 |
| (13) preservative | suitable amount |
| (14) colorant | suitable amount |
| (15) perfume | suitable amount |
| (16) purified water | balance |

<Method for Preparation>

The humectant and colorant were added to purified water, and the temperature of the resultant solution was adjusted to 70° C. with heat (aqueous phase). The surfactant and the preservative were added to the oily components, and the temperature of the resultant mixture was adjusted to 70° C. with heat. The mixture was added to the aqueous phase, and the resultant mixture was subjected to preliminary emulsification. Xyloglucan and ethanol were added to the emulsion followed by stirring. The emulsified particles of the emulsion were homogenized by use of a homogenization mixer. Thereafter, the emulsion was degassed, filtered, and cooled to thereby obtain the desired milky lotion.

Example B8
Foundation

| | amount (wt. %) |
|---|---|
| (1) talc | 3.0 |
| (2) titanium dioxide | 5.0 |
| (3) red iron oxide | 0.5 |
| (4) yellow iron oxide | 1.4 |
| (5) black iron oxide | 0.1 |
| (6) polyoxyethylene sorbitan monostearate | 0.9 |
| (7) triethanolamine | 1.0 |
| (8) propylene glycol | 5.0 |
| (9) agar | 0.5 |
| (10) xyloglucan | 0.5 |
| (11) stearic acid | 2.2 |
| (12) isohexadecyl alcohol | 7.0 |
| (13) glyceryl monostearate | 2.0 |
| (14) liquid lanolin | 2.0 |
| (15) liquid paraffin | 8.0 |
| (16) preservative | suitable amount |
| (17) perfume | suitable amount |
| (18) purified water | 60.9 |

<Method for Preparation>

The xyloglucan was dispersed in the propylene glycol, and the mixture was added to the purified water. The resultant solution was mixed at 70° C. by use of a homogenization mixer, and the remaining components of the aqueous phase were added thereto and stirred sufficiently. The powder components were mixed and crushed sufficiently, and added to the aqueous phase with stirring. The resultant mixture was mixed at 70° C. by use of a homogenization mixer. The mixture was cooled with stirring, and the perfume was added thereto at 45° C. Thereafter, the resultant mixture was degassed and filled in a container to thereby obtain the desired foundation.

Example B9
Acidic Hair Dye

| | amount (wt. %) |
|---|---|
| (1) acid dye | 1.0 |
| (2) benzyl alcohol | 6.0 |
| (3) isopropyl alcohol | 20.0 |
| (4) citric acid | 0.3 |
| (5) xyloglucan | 2.0 |
| (6) locust bean gum | 2.0 |
| (7) purified water | 68.7 |

<Method for Preparation>

All components are homogeneously mixed to thereby obtain the desired acidic hair dye. In this method, xyloglucan and locust bean gum were dispersed in benzyl alcohol, and the resultant mixture was mixed with the remaining components.

Example B10
Lipstick

| | amount (wt. %) |
|---|---|
| (1) titanium dioxide | 4.5 |
| (2) Red #201 | 0.5 |
| (3) Red #202 | 2.0 |
| (4) Red #223 | 0.05 |
| (5) ceresin | 4.0 |
| (6) candelilla wax | 8.0 |
| (7) carnauba wax | 2.0 |
| (8) castor oil | 30.0 |
| (9) glyceryl diisostearate | 37.95 |
| (10) POE (25) POP (20) 2-tetradecyl ether | 1.0 |
| (11) purified water | balance |
| (12) glycerin | 2.0 |
| (13) xyloglucan | 0.5 |
| (14) propylene glycol | 1.0 |
| (15) tragacanth gum | 2.0 |
| (16) antioxidant | suitable amount |
| (17) perfume | suitable amount |

<Method for Preparation>

The titanium dioxide, the Red #201, and the Red #202 were added to a portion of the castor oil, and the resultant mixture was processed by a roller (pigment portion). The Red #223 was dissolved in the remaining portion of the castor oil (dye portion). The purified water, glycerin, xyloglucan, tragacanth gum, and propylene glycol were homogeneously dissolved at 80° C. (aqueous phase). The remaining components were mixed and dissolved with heat. The pigment portion and the dye portion were added thereto, and the resultant mixture was homogeneously dispersed by use of a homogenization mixer. The aqueous phase was added thereto, and the resultant mixture was dispersed and emulsified by use of the homogenization mixer. Thereafter, the resultant emulsion was poured in a stick-shaped mold and cooled immediately to thereby obtain the desired lipstick.

Example B11
Shampoo

| | amount (wt. %) |
|---|---|
| (1) sodium POE (3) lauryl sulfate (30% aqueous solution) | 30.0 |
| (2) sodium lauryl sulfate (30% aqueous solution) | 10.0 |
| (3) coconut fatty acid diethanolamide | 4.0 |
| (4) glycerin | 1.0 |
| (5) xyloglucan | 2.0 |
| (6) hydroxyethylcellulose | 0.5 |
| (7) perfume | suitable amount |
| (8) pigment | suitable amount |
| (9) preservative | suitable amount |
| (10) sequestering agent, pH controller | suitable amount |
| (11) purified water | balance |

<Method for Preparation>

The purified water was heated, and the temperature thereof was adjusted to 70° C. The remaining components were added thereto and homogeneously dissolved. Thereafter, the resultant mixture was cooled to thereby obtain the desired shampoo.

Example B12
Rinse

|  | amount (wt. %) |
| --- | --- |
| (1) silicone oil | 3.0 |
| (2) liquid paraffin | 1.0 |
| (3) cetyl alcohol | 1.5 |
| (4) stearyl alcohol | 1.0 |
| (5) stearyl trimethylammonium chloride | 0.7 |
| (6) glycerin | 3.0 |
| (7) xyloglucan | 1.0 |
| (8) tragacanth gum | 0.1 |
| (9) perfume | suitable amount |
| (10) pigment | suitable amount |
| (11) preservative | suitable amount |
| (12) purified water | balance |

<Method for Preparation>

The xyloglucan, tragacanth gum, stearyl-trimethylammonium chloride, glycerin, and pigment were added to the purified water, and the temperature of the resultant mixture was maintained at 70° C. (aqueous phase). The remaining components were mixed and dissolved with heat. The temperature of the resultant mixture was maintained at 70° C. (oil phase). The oil phase was added to the aqueous phase, and the resultant mixture was emulsified by use of a homogenization mixer. Thereafter, the resultant emulsion was cooled with stirring to thereby obtain the desired rinse.

Example B13
Rinse-combined Shampoo

|  | amount (wt. %) |
| --- | --- |
| (1) imidazoliniumbetaine-type amphoteric surfactant | 16.0 |
| (2) coconut fatty acid diethanolamide | 4.0 |
| (3) stearyl trimethylammonium chloride | 2.0 |
| (4) sodium N-lauroyl-N-methyl-β-aminopropionate | 1.0 |
| (5) silicone derivative | 1.0 |
| (6) polyoxyethylene alkylpolyamine | 1.0 |
| (7) xyloglucan | 1.5 |
| (8) locust bean gum | 0.1 |
| (9) perfume | suitable amount |
| (10) pigment | suitable amount |
| (11) preservative | suitable amount |
| (12) pH controller | suitable amount |
| (13) purified water | balance |

<Method for Preparation>

The xyloglucan, locust bean gum, stearyl-trimethylammonium chloride, and amphoteric surfactant were added to the purified water, dissolved with heat, and the temperature of the mixture was maintained at 70° C. The remaining components were added thereto and dissolved. Thereafter, the resultant mixture was cooled to thereby obtain the desired rinse-combined shampoo.

C. Examples of a Third Mode of the Present Invention

Prior to disclosure of formulation examples, evaluation methods applied to the external-use compositions of the present invention are first described.

1. Sensory Analysis of Sensation in Use

For sensory analysis of sensation in use, each test composition was judged by 60 panelists; 30 men and 30 women. Fit for the skin, sticky sensation in use, and smooth sensation in use of each test composition were judged on the basis of the number of panelists who reported such sensations, and evaluation standards are as follows.

Evaluation Standards for Fit for the Skin

A: 30 or more panelists have reported good fit for the skin
B: at least 10 and less than 30 panelists have reported good fit for the skin
C: at least 5 and less than 10 panelists have reported good fit for the skin
D: less than 5 panelists have reported good fit for the skin Evaluation Standards for Sticky Sensation in Use A: 30 or more panelists have reported no sticky sensation
B: at least 10 and less than 30 panelists have reported no sticky sensation
C: at least 5 and less than 10 panelists have reported no sticky sensation
D: less than 5 panelists have reported no sticky sensation Evaluation Standards for Smooth Sensation in Use A: 30 or more panelists have reported a smooth sensation
B: at least 10 and less than 30 panelists have reported a smooth sensation
C: at last 5 and less than 10 panelists have reported a smooth sensation
D: less than 5 panelists have reported a smooth sensation

2. Evaluation of Moisture Retention by Moisture Evaporation Rate

Measurement of moisture evaporation is suitable for evaluating moisture retention.

A sample solution (10 μl) was added dropwise to a filter paper (2.0×2.0 cm) and the weight loss of the sample was measured at 1 min. intervals for 10 minutes to thereby obtain the weight loss per minute.

Evaluation Standards for Moisture Retention

A: moisture evaporation rate was less than 0.5 μg/min.
B: moisture evaporation rate was at least 0.5 μg/min. and less than 0.55 μg/min.
C: moisture evaporation rate was at least 0.55 μg/min. and less than 0.60 μg/min.
D: moisture evaporation rate was 0.60 4μg/min. or more First, lotions whose formulas were described in the following Comparative Examples C1 to C6 (Table C1) and Examples C1 to C6 (Table C2) were prepared through conventional methods.

TABLE C1

| | Amount (wt. %) Comparative Example | | | | | |
| --- | --- | --- | --- | --- | --- | --- |
| | C1 | C2 | C3 | C4 | C5 | C6 |
| (1) glycerin | 10.0 | — | — | — | — | — |
| (2) 1,3-butylene glycol | 4.0 | 4.0 | 4.0 | 4.0 | 4.0 | 4.0 |
| (3) POE (20) oleyl alcohol ether | 0.5 | 0.5 | 0.5 | 0.5 | 0.5 | 0.5 |
| (4) xyloglucan | — | — | 2.0 | — | — | — |
| (5) hydroxyethylcellulose | — | — | — | 2.0 | — | — |
| (6) xanthan gum | — | — | — | — | 2.0 | — |
| (7) sericin | — | — | — | — | — | 2.0 |
| (8) preservative | s.a. | s.a. | s.a. | s.a. | s.a. | s.a. |
| (9) perfume | s.a. | s.a. | s.a. | s.a. | s.a. | s.a. |
| (10) purified water | bal. | bal. | bal. | bal. | bal. | bal. | s.a.; suitable amount   bal.; balance

TABLE C2

|  | Amount (wt. %) Example | | | | | |
|---|---|---|---|---|---|---|
|  | C1 | C2 | C3 | C4 | C5 | C6 |
| (1) 1,3-butylene glycol | 4.0 | 4.0 | 4.0 | 4.0 | 4.0 | 4.0 |
| (2) POE (20) oleyl alcohol ether | 0.5 | 0.5 | 0.5 | 0.5 | 0.5 | 0.5 |
| (3) xyloglucan | 2.0 | 2.0 | 2.0 | 0.1 | 2.0 | 0.1 |
| (4) hydroxyethylcellulose | 1.0 | 1.0 | 0.1 | 2.0 | — | 0.1 |
| (5) xanthan gum | 1.0 | 1.0 | — | — | 0.1 | 0.1 |
| (6) sericin | 1.0 | 0.1 | 1.0 | 1.0 | 1.0 | 1.0 |
| (7) preservative | s.a. | s.a. | s.a. | s.a. | s.a. | s.a. |
| (8) perfume | s.a. | s.a. | s.a. | s.a. | s.a. | s.a. |
| (9) purified water | bal. | bal. | bal. | bal. | bal. | bal. | s.a; suitable amount    bal.; balance

These test compositions were tested by sensory analysis of sensation in use and evaluation of moisture retention.

The results were described in the following Table C3 (Comparative Examples) and Table C4 (Examples).

TABLE C3

|  | Comparative Example | | | | | |
|---|---|---|---|---|---|---|
|  | C1 | C2 | C3 | C4 | C5 | C6 |
| sensation in use |  |  |  |  |  |  |
| fit for the skin | C | C | A | C | C | B |
| sticky sensation in use | D | C | B | B | C | C |
| smooth sensation in use | C | C | A | B | C | B |
| moisture retention | A | D | B | C | C | C |

TABLE C4

|  | Example | | | | | |
|---|---|---|---|---|---|---|
|  | C1 | C2 | C3 | C4 | C5 | C6 |
| sensation in use |  |  |  |  |  |  |
| fit for the skin | A | A | A | A | A | A |
| sticky sensation in use | A | A | A | A | A | A |
| smooth sensation in use | A | A | A | A | A | B |
| moisture retention | A | A | A | B | A | A |

As shown in Table C3 and Table C4, incorporation of xyloglucan, a thickening polysaccharide, and sericin has a synergistic effect, thus yielding an external-use composition having superior moisture retention and advantageous sensation in use.

A variety of product forms of the external-use compositions of a third mode of the present invention are described in the following examples. External-use compositions of the third mode of the present invention were tested through the above "sensory analysis of sensation in use" and "evaluation of moisture retention." In both evaluations, the compositions of the Examples were ranked "A" or "B" of the above standards.

Example C7
Cream

|  | amount (wt. %) |
|---|---|
| (1) cetyl alcohol | 5.0 |
| (2) stearic acid | 3.0 |
| (3) vaseline | 5.0 |
| (4) squalane | 10.0 |
| (5) glyceryl tri-2-ethylhexanoate | 7.0 |
| (6) dipropylene glycol | 5.0 |
| (7) glycerin | 5.0 |
| (8) propyleneglycol monostearate | 1.5 |
| (9) POE (20) cetyl alcohol ether | 1.5 |
| (10) triethanolamine | 1.0 |
| (11) xyloglucan | 1.0 |
| (12) hydroxyethylcellulose | 1.0 |
| (13) sericin | 0.5 |
| (14) preservative | suitable amount |
| (15) antioxidant | suitable amount |
| (16) perfume | suitable amount |
| (17) purified water | balance |

<Method for Preparation>

The humectant and alkali were added to the purified water, and the temperature of the resultant solution was adjusted to 70° C. (aqueous phase). The oily components were dissolved with heat. The surfactant, preservative, antioxidant, and perfume were added thereto and the temperature of the resultant mixture was adjusted to 70° C. The mixture was added to the aqueous phase and the resultant mixture was subjected to preliminary emulsification. The emulsified particles of the emulsion were homogenized by use of a homogenization mixer. Thereafter, the emulsion was degassed, filtered, and cooled to thereby obtain the desired cream.

Example C8
Milky Lotion

|  | amount (wt. %) |
|---|---|
| (1) cetyl alcohol | 1.0 |
| (2) beeswax | 0.5 |
| (3) vaseline | 2.0 |
| (4) squalane | 6.0 |
| (5) dimethylpolysiloxane | 2.0 |
| (6) ethanol | 5.0 |
| (7) glycerin | 4.0 |
| (8) 1,3-butylene glycol | 4.0 |
| (9) POE (10) monooleic acid ester | 1.0 |
| (10) glyceryl monostearate | 1.0 |
| (11) xyloglucan | 2.0 |
| (12) xanthan gum | 0.1 |
| (13) sericin | 1.0 |
| (14) preservative | suitable amount |
| (15) colorant | suitable amount |
| (16) perfume | suitable amount |
| (17) purified water | balance |

<Method for Preparation>

The humectant and the colorant were added to the purified water and the temperature of the resultant solution was adjusted to 70° C. (aqueous phase). Subsequently, the surfactant and the preservative were added to the oily components, and the temperature of the resultant mixture was adjusted to 70° C. The mixture was added to the aqueous phase and the resultant mixture was subjected to preliminary emulsification. To the resultant emulsified product were added xyloglucan and ethanol, and the mixture was stirred and homogenized with a homogenization mixer until uniform emulsion particles were obtained. Thereafter, the emulsion was degassed, filtered, and cooled to thereby obtain the desired milky lotion.

Example C9

Foundation

|  | amount (wt. %) |
|---|---|
| (1) talc | 3.0 |
| (2) titanium dioxide | 5.0 |
| (3) red iron oxide | 0.5 |
| (4) yellow iron oxide | 1.4 |
| (5) black iron oxide | 0.1 |
| (6) polyoxyethylene sorbitan monostearate | 0.9 |
| (7) triethanolamine | 1.0 |
| (8) propylene glycol | 5.0 |
| (9) hydroxyethylcellulose | 0.5 |
| (10) xyloglucan | 0.5 |
| (11) sericin | 0.5 |
| (12) stearic acid | 2.2 |
| (13) isohexadecyl alcohol | 7.0 |
| (14) glyceryl monostearate | 2.0 |
| (15) liquid lanolin | 2.0 |
| (16) liquid paraffin | 8.0 |
| (17) preservative | suitable amount |
| (18) perfume | suitable amount |
| (19) purified water | balance |

<Method for Preparation>

The xyloglucan was dispersed in the propylene glycol, and the mixture was added to the purified water. The resultant solution was mixed at 70° C. by use of a homogenization mixer, and the remaining components of the aqueous phase were added thereto and stirred sufficiently. The components of the powdery portion were mixed and crushed sufficiently, and added to the aqueous phase with stirring. The resultant mixture was mixed at 70° C. by use of a homogenization mixer. The mixture was cooled with stirring, and the perfume was added thereto at 45° C. Thereafter, the resultant mixture was degassed and filled in a container to thereby obtain the desired foundation.

D. Examples of a Fourth Mode of the Present Invention

Prior to disclosure of formulation examples, evaluation methods applied to the external-use compositions of the present invention are first described.

1. Sensory Analysis of Sensation in Use

Each test composition was compared with a comparative composition in terms of sensation in use, by 60 panelists; 30 men and 30 women, and sensation in use of each test composition was judged on the basis of the following standards.

Evaluation Standards

A: 40 or more panelists have evaluated the test composition as better than the comparative composition B: at least 20 and less than 40 panelists have evaluated the test composition as better than the comparative composition C: at least 10 and less than 20 panelists have evaluated the test composition as better than the comparative composition D: less than 10 panelists have evaluated the test composition as better than the comparative composition

2. Evaluation of Viscosity Stability (Evaluation of Salt Tolerance)

In Examples D1 to D3 and Comparative Example D1, the difference in viscosity between a sodium-chloride-added composition and a sodium-chloride-free composition was evaluated by measurement of viscosity of each test composition immediately after preparation, by use of a B-type viscometer. The measurement of viscosity was conducted at 25° C.

In the test, sodium chloride was added in an amount of 1.0 wt. % with respect to the entirety of the composition after the addition of the carboxyvinylpolymer and xyloglucan.

In the following examples, "GLYROID 6C" of Dainippon Pharmaceutical Co., Ltd. was used as xyloglucan.

Example D1

|  | amount (wt. %) |
|---|---|
| (1) purified water | balance |
| (2) 1,3-butyleneglycol | 5.0 |
| (3) carboxyvinylpolymer | 0.1 |
| (4) xyloglucan | 0.5 |
| (5) glyceryl monostearate | 0.5 |
| (6) POE (10) monooleic acid ester | 0.5 |
| (7) liquid paraffin | 5.0 |
| (8) potassium hydroxide | 0.1 |
| (9) preservative | 0.1 |
| (10) chelating agent | suitable amount |
| (11) antioxidant | suitable amount |
| (12) perfume | suitable amount |

Example D2

Milky Lotion

|  | amount (wt. %) |
|---|---|
| (1) purified water | balance |
| (2) 1,3-butylene glycol | 5.0 |
| (3) carboxyvinylpolymer | 0.1 |
| (4) xyloglucan | 5.0 |
| (5) glyceryl monostearate | 0.5 |
| (6) POE (10) monooleic acid ester | 0.5 |
| (7) liquid paraffin | 5.0 |
| (8) potassium hydroxide | 0.1 |
| (9) preservative | 0.1 |
| (10) chelating agent | suitable amount |
| (11) antioxidant | suitable amount |
| (12) perfume | suitable amount |

Example D3

Milky Lotion

|  | amount (wt. %) |
|---|---|
| (1) purified water | balance |
| (2) 1,3-butylene glycol | 5.0 |
| (3) carboxyvinylpolymer | 0.1 |
| (4) xyloglucan | 0.01 |
| (5) glyceryl monostearate | 0.5 |
| (6) POE (10) monooleic acid ester | 0.5 |
| (7) liquid paraffin | 5.0 |
| (8) potassium hydroxide | 0.1 |
| (9) preservative | 0.1 |
| (10) chelating agent | suitable amount |
| (11) antioxidant | suitable amount |
| (12) perfume | suitable amount |

Comparative Example D1

Milky Lotion

|  | amount (wt. %) |
| --- | --- |
| (1) purified water | balance |
| (2) 1,3-butylene glycol | 5.0 |
| (3) carboxyvinylpolymer | 0.1 |
| (4) glyceryl monostearate | 0.5 |
| (5) POE (10) monooleic acid ester | 0.5 |
| (6) liquid paraffin | 5.0 |
| (7) potassium hydroxide | 0.1 |
| (8) preservative | 0.1 |
| (9) chelating agent | suitable amount |
| (10) antioxidant | suitable amount |
| (11) perfume | suitable amount |

<Method for Preparation>

The test compositions of Examples D1 to D3 and Comparative Example D1 were prepared as follows.

The humectant and the chelating agent were added to the purified water and heated to 70° C., to thereby prepare an aqueous phase. Independently, the liquid paraffin, surfactant, preservative, and perfume were mixed with heat at 70° C. The resultant mixture was added to the aqueous phase, and the obtained mixture was subjected to preliminary emulsification. The carboxyvinylpolymer and xyloglucan were added thereto followed by stirring, and the emulsified particles of the resultant emulsion were homogenized by use of a homogenization mixer. Thereafter, the emulsion was degassed, filtered, and cooled to thereby obtain the respective test composition.

Milky lotions of the Examples and the Comparative Example were prepared through the above method, and these lotions were tested through a sensory analysis of sensation in use and evaluation of viscosity stability as described above. The results are described in the following Table D1 (sensory analysis of sensation in use) and Table D2 (evaluation of viscosity stability).

TABLE D1

| Item | Example D1 | Example D2 | Example D3 | Comparative Example D1 |
| --- | --- | --- | --- | --- |
| Sensation in use | A | C | D | control |

The results of Table D1 show that the external-use composition of the fourth mode of the present invention, which incorporates xyloglucan and carboxyvinylpolymer in a suitable amount (Example D1), has greatly improved sensation in use as compared with a composition of Comparative Example D1, which incorporates carboxyvinylpolymer and does not incorporate xyloglucan.

TABLE D2

| Item | Example D1 | Example D2 | Example D3 | Comparative Example D3 |
| --- | --- | --- | --- | --- |
| NaCl-free | 3560 cps | 25000 cps | 2700 cps | 2500 cps |
| NaCl-added | 3600 cps | 26000 cps | 450 cps | 300 cps |

The results of Table D2 show that the external-use composition of the fourth mode of the present invention, which incorporates xyloglucan and carboxyvinylpolymer, is superior in salt tolerance when the amount of xyloglucan is more than 0.05 wt. % with respect to the entirety of the composition (Examples D1 and D2).

A variety of product forms of the external-use compositions of the fourth mode of the present invention are described in the following examples. The external-use compositions of the fourth mode of the present invention were tested through the above two methods, and every composition of the fourth mode of the present invention was found to be significantly superior in sensation in use and salt tolerance to the composition of the corresponding comparative example, which does not incorporate xyloglucan.

Example D4

Cream

|  | amount (wt. %) |
| --- | --- |
| (1) purified water | balance |
| (2) 1,3-butylene glycol | 8.0 |
| (3) carboxyvinylpolymer | 0.1 |
| (4) xyloglucan | 1.0 |
| (5) POE (10) monooleic acid ester | 1.0 |
| (6) glyceryl monostearate | 1.0 |
| (7) cetyl alcohol | 1.0 |
| (8) beeswax | 0.5 |
| (9) vaseline | 2.0 |
| (10) squalane | 6.0 |
| (11) dimethylpolysiloxane | 2.0 |
| (12) potassium hydroxide | 0.1 |
| (13) preservative | suitable amount |
| (14) colorant | suitable amount |
| (15) chelating agent | suitable amount |
| (16) perfume | suitable amount |

<Method for Preparation>

The humectant and colorant ingredients were added to the purified water, and the temperature of the resultant solution was adjusted to 70° C. so as to prepare an aqueous phase. The surfactant and the preservative were added to the oily components, and the temperature of the resultant mixture was adjusted to 70° C. with heat. The mixture was added to the aqueous phase, and the resultant mixture was subjected to preliminary emulsification. The carboxyvinylpolymer and xyloglucan were added to the resultant emulsion followed by stirring, and the emulsified particles of the emulsion were homogenized by use of a homogenization mixer. Thereafter, the emulsion was degassed, filtered, and cooled to thereby obtain the desired cream.

Example D5

Lotion

|  | amount (wt. %) |
| --- | --- |
| (1) purified water | balance |
| (2) dipropylene glycol | 10.0 |
| (3) PEG 1500 | 5.0 |
| (4) carboxyvinylpolymer | 0.1 |
| (5) xyloglucan | 0.05 |
| (6) POE (20) oleyl alcohol ether | 0.5 |
| (7) ethanol | 5.0 |
| (8) potassium hydroxide | 0.1 |
| (9) perfume | suitable amount |
| (10) colorant | suitable amount |
| (11) preservative | suitable amount |
| (12) chelating agent | suitable amount |
| (13) anti-fading agent | suitable amount |

<Method for Preparation>

The chelating agent was dissolved in a portion of the purified water, and the carboxyvinylpolymer and xyloglucan were added thereto, followed by mixing and stirring. The humectant, anti-fading agent, etc. were dissolved in the remaining portion of the purified water at room temperature, and the previously prepared solution was added thereto so as to obtain an uniform aqueous solution. Separately, the preservative, surfactant, and perfume were added to the ethanol so as to obtain an alcoholic solution, and the alcoholic solution was mixed in the aqueous solution so as to solubilize the aqueous phase. Thereafter, the color of the resultant mixture was adjusted with the colorant, and the mixture was filtered to thereby obtain the desired lotion.

Example D6

Pack

|  | amount (wt. %) |
| --- | --- |
| (1) purified water | balance |
| (2) PEG 1500 | 5.0 |
| (3) dipropylene glycol | 5.0 |
| (4) sorbitol | 5.0 |
| (5) carboxyvinylpolymer | 1.0 |
| (6) xyloglucan | 4.0 |
| (7) POE lauryl ether | 1.0 |
| (8) ethanol | 5.0 |
| (9) potassium hydroxide | 0.5 |
| (10) perfume | suitable amount |
| (11) preservative | suitable amount |

<Method for Preparation>

The carboxyvinylpolymer and xyloglucan were dissolved in a portion of the purified water with stirring (aqueous phase). Separately, the perfume, the preservative, and the surfactant were dissolved in the ethanol, and the resultant solution was added to the aqueous phase so as to solubilize the aqueous phase. Finally, the potassium hydroxide was added to the remaining portion of the purified water, the solubilized portion was added thereto, and the resultant mixture was neutralized and degassed, followed by filtration, to thereby obtain the desired pack.

Example D7

Hair Dye

|  | amount (wt. %) |
| --- | --- |
| (1) purified water | 67.7 |
| (2) benzyl alcohol | 6.0 |
| (3) isopropyl alcohol | 20.0 |
| (4) carboxyvinylpolymer | 0.5 |
| (5) xyloglucan | 4.0 |
| (6) citric acid | 0.3 |
| (7) potassium hydroxide | 0.5 |
| (8) acid dye | 1.0 |

<Method for Preparation>

All components are homogeneously mixed to thereby obtain the desired acidic hair dye. In this method, the carboxyvinylpolymer and xyloglucan were dispersed in the benzyl alcohol, and the resultant mixture was mixed with the remaining components.

Example D8

Sunscreen Agent

|  | amount (wt. %) |
| --- | --- |
| (aqueous phase) |  |
| (1) purified water | balance |
| (2) dipropylene glycol | 6.0 |
| (3) carboxyvinylpolymer | 0.1 |
| (4) xyloglucan | 0.5 |
| (5) potassium hydroxide | 0.1 |
| (oil phase) |  |
| (6) octyl p-methoxycinnamate | 6.0 |
| (7) glyceryl octyl di-p-methoxycinnamate | 2.0 |
| (8) 4-tert-butyl-4'-methoxybenzoylmethane | 2.0 |
| (9) oxybenzone | 3.0 |
| (10) oleyl oleate | 5.0 |
| (11) dimethylpolysiloxane | 3.0 |
| (12) vaseline | 0.5 |
| (13) cetyl alcohol | 1.0 |
| (14) sorbitan ester of sesquioleic acid | 0.8 |
| (15) POE (20) oleyl alcohol ether | 1.2 |
| (16) antioxidant | suitable amount |
| (17) preservative | suitable amount |
| (18) perfume | suitable amount |

<Method for Preparation>

The oil phase and the aqueous phase were separately heated and dissolved at 70° C. The oil phase was added to the aqueous phase, and the resultant mixture was emulsified by use of a homogenizer. The resultant emulsion was cooled by use of a heat exchanger to thereby obtain the desired sunscreen agent.

E. Examples of a Fifth Mode of the Present Invention

Prior to disclosure of formulation examples, evaluation methods applied to the external-use composition of the fifth mode of the present invention are first described.

1. Sensory Analysis of Sensation in Use

Sensation in use of each test composition was judged by 60 panelists; 30 men and 30 women. Sensation in use was judged on the basis of the number of panelists who reported poor fit for the skin. Evaluation standards are as follows.

Evaluation Standards

A: less than 5 panelists have reported poor fit for the skin
B: at least 5 and less than 10 panelists have reported poor fit for the skin
C: at least 10 and less than 30 panelists have reported poor fit for the skin
D: 30 or more panelists have reported poor fit for the skin 2. Evaluation of Viscosity Stability (Evaluation of Salt Tolerance)

In Examples E1 to E6 and Comparative Examples E1 and E2, the difference in viscosity between a sodium-chloride-added composition and a sodium-chloride-free composition was calculate d by measuring viscosity of each test composition immediately after preparation, by use of a B-type viscometer. The measurement of viscosity was conducted at 25° C.

In this test, sodium chloride was added in an amount of 1.0 wt. % with respect to the entirety of the composition after the addition of the alkyl-modified carboxyvinylpolymer and xyloglucan.

In the following examples, "GLYROID 6C" of Dainippon Pharmaceutical Co., Ltd. was used as xyloglucan.

Example E1
Milky Lotion

| | amount (wt. %) |
|---|---|
| (1) purified water | balance |
| (2) 1,3-butylene glycol | 5.0 |
| (3) xyloglucan | 2.0 |
| (4) alkyl-modified carboxyvinylpolymer | 0.2 |
| (5) octamethylcyclotetrasiloxane | 3.0 |
| (6) liquid paraffin | 2.0 |
| (7) macadamia nut oil | 3.0 |
| (8) silicic acid anhydride | 0.5 |
| (9) potassium hydroxide | 0.1 |
| (10) antioxidant | suitable amount |
| (11) preservative | suitable amount |
| (12) perfume | suitable amount |

Example E2
Milky Lotion

| | amount (wt. %) |
|---|---|
| (1) purified water | balance |
| (2) 1,3-butylene glycol | 5.0 |
| (3) xyloglucan | 2.0 |
| (4) alkyl-modified carboxyvinylpolymer | 0.2 |
| (5) highly polymerized dimethylsiloxane. methyl(aminopropyl)siloxane copolymer | 3.0 |
| (6) liquid paraffin | 2.0 |
| (7) macadamia nut oil | 3.0 |
| (8) silicic acid anhydride | 0.5 |
| (9) potassium hydroxide | 0.1 |
| (10) antioxidant | suitable amount |
| (11) preservative | suitable amount |
| (12) perfume | suitable amount |

Example E3
Milky Lotion

| | amount (wt. %) |
|---|---|
| (1) purified water | balance |
| (2) 1,3-butylene glycol | 5.0 |
| (3) xyloglucan | 2.0 |
| (4) alkyl-modified carboxyvinylpolymer | 0.2 |
| (5) highly polymerized dimethylpolysiloxane | 3.0 |
| (6) liquid paraffin | 2.0 |
| (7) macadamia nut oil | 3.0 |
| (8) silicic acid anhydride | 0.5 |
| (9) potassium hydroxide | 0.1 |
| (10) antioxidant | suitable amount |
| (11) preservative | suitable amount |
| (12) perfume | suitable amount |

Example E4
Milky Lotion

| | amount (wt. %) |
|---|---|
| (1) purified water | balance |
| (2) 1,3-butylene glycol | 5.0 |
| (3) xyloglucan | 2.0 |
| (4) alkyl-modified carboxyvinylpolymer | 0.2 |
| (5) methylpolysiloxane | 3.0 |
| (6) liquid paraffin | 2.0 |
| (7) macadamia nut oil | 3.0 |
| (8) silicic acid anhydride | 0.5 |
| (9) potassium hydroxide | 0.1 |
| (10) antioxidant | suitable amount |
| (11) preservative | suitable amount |
| (12) perfume | suitable amount |

Example E5
Milky Lotion

| | amount (wt. %) |
|---|---|
| (1) purified water | balance |
| (2) 1,3-butylene glycol | 5.0 |
| (3) xyloglucan | 2.0 |
| (4) alkyl-modified carboxyvinylpolymer | 0.2 |
| (5) methylphenyl polysiloxane | 3.0 |
| (6) liquid paraffin | 2.0 |
| (7) macadamia nut oil | 3.0 |
| (8) silicic acid anhydride | 0.5 |
| (9) potassium hydroxide | 0.1 |
| (10) antioxidant | suitable amount |
| (11) preservative | suitable amount |
| (12) perfume | suitable amount |

Example E6
Milky Lotion

| | amount (wt. %) |
|---|---|
| (1) purified water | balance |
| (2) 1,3-butylene glycol | 5.0 |
| (3) xyloglucan | 2.0 |
| (4) alkyl-modified carboxyvinylpolymer | 0.2 |
| (5) liquid paraffin | 2.0 |
| (6) macadamia nut oil | 3.0 |
| (7) silicic acid anhydride | 0.5 |
| (8) potassium hydroxide | 0.1 |
| (9) antioxidant | suitable amount |
| (10) preservative | suitable amount |
| (11) perfume | suitable amount |

Comparative Example E1
Milky Lotion

| | amount (wt. %) |
|---|---|
| (1) purified water | balance |
| (2) 1,3-butylene glycol | 5.0 |
| (3) alkyl-modified carboxyvinylpolymer | 0.2 |
| (4) methylphenyl polysiloxane | 3.0 |
| (5) liquid paraffin | 2.0 |
| (6) macadamia nut oil | 3.0 |
| (7) silicic acid anhydride | 0.5 |
| (8) potassium hydroxide | 0.1 |
| (9) antioxidant | suitable amount |
| (10) preservative | suitable amount |
| (11) perfume | suitable amount |

Comparative Example E2
Milky Lotion

| | amount (wt. %) |
|---|---|
| (1) purified water | balance |
| (2) 1,3-butylene glycol | 5.0 |
| (3) alkyl-modified carboxyvinylpolymer | 0.2 |
| (4) liquid paraffin | 2.0 |
| (5) macadamia nut oil | 3.0 |
| (6) silicic acid anhydride | 0.5 |
| (7) potassium hydroxide | 0.1 |
| (8) antioxidant | suitable amount |
| (9) preservative | suitable amount |
| (10) perfume | suitable amount |

<Method for Preparation>

Each test composition of Examples E1 to E6 and Comparative Examples E1 and E2 was prepared as follows; the oil phase was added to the aqueous phase with emulsifying by use of a emulsifier to thereby obtain a composition.

Milky lotions of the examples and the comparative examples were prepared through the above method, and these lotions were tested through the above sensory analysis of sensation in use and evaluation of viscosity stability. The results are described in the following Table E1 (sensory analysis of sensation in use) and Table E2 (evaluation of viscosity stability).

TABLE E1

| | Example | | | | | | Comparative Example | |
|---|---|---|---|---|---|---|---|---|
| Item | E1 | E2 | E3 | E4 | E5 | E6 | E1 | E2 |
| Sensation in use | A | A | A | B | B | C | C | D |

The results in Table E1 show that the external-use composition of the present invention, which incorporates xyloglucan and an alkyl-modified carboxyvinylpolymer, is superior to the test compositions of the comparative examples in terms of sensation in use. The results also show that if a silicone derivative is added simultaneously, the sensation of use is further improved.

TABLE E2

| Item | Example E1 | Example E2 | Example E3 | Example E4 |
|---|---|---|---|---|
| NaCl-free | 2850 cps | 2750 cps | 3000 cps | 2800 cps |
| NaCl-added | 2900 cps | 2700 cps | 3100 cps | 2840 cps |

| Item | Example E5 | Example E6 | Comparative Example E1 | Comparative Example E2 |
|---|---|---|---|---|
| NaCl-free | 2800 cps | 2700 cps | 2650 cps | 2560 cps |
| NaCl-added | 2850 cps | 2750 cps | 250 cps | 200 cps |

The results of Table E2 show that the external-use compositions of the fifth mode of the present invention have superior salt tolerance.

A variety of product forms of the external-use compositions of the fifth mode of the present invention are be described in the following examples. The external-use compositions of the fifth mode of the present invention were tested through the above methods, and every composition of the fifth mode of the present invention was found to be significantly superior to the composition of the corresponding comparative example, which does not incorporate xyloglucan.

Example E7
Cream

| | amount (wt. %) |
|---|---|
| (aqueous phase) | |
| (1) purified water | balance |
| (2) 1,3-butylene glycol | 6.0 |
| (3) PEG 1500 | 4.0 |
| (4) xyloglucan | 1.0 |
| (5) dimethylsiloxane. methyl(polyoxyethylene)siloxane copolymer | 1.0 |
| (6) alkyl-modified carboxyvinylpolymer | 0.1 |
| (oil phase) | |
| (7) stearyl alcohol | 3.0 |
| (8) hydrogenated lanolin | 3.0 |
| (9) squalane | 5.0 |
| (10) octyldodecanol | 8.0 |
| (11) preservative | suitable amount |
| (12) antioxidant | suitable amount |
| (13) perfume | suitable amount |

<Method for Preparation>

The humectant was added to the purified water, and the resultant solution was heated to 70° C. to prepare an aqueous phase. The oily components were dissolved with heat, followed by addition of the preservative, the antioxidant, and the perfume. The temperature of the resultant mixture was adjusted to 70° C. The mixture was added to the aqueous phase, and the emulsified particles of the resultant mixture were homogenized by use of a homogenization mixer. Thereafter, the emulsion was degassed, filtered, and cooled to thereby obtain the desired cream.

Example E8
Lotion

| | amount (wt. %) |
|---|---|
| (1) purified water | balance |
| (2) 1,3-butylene glycol | 6.0 |
| (3) glycerin | 5.0 |
| (4) PEG 4000 | 3.0 |
| (5) xyloglucan | 0.1 |
| (6) octamethylcyclotetrasiloxane | 0.05 |
| (7) alkyl-modified carboxyvinylpolymer | 0.05 |
| (8) ethanol | 5.0 |
| (9) olive oil | 0.5 |
| (10) perfume | suitable amount |
| (11) colorant | suitable amount |
| (12) preservative | suitable amount |
| (13) anti-fading agent | suitable amount |

<Method for Preparing>

The humectant, anti-fading agent, and xyloglucan were dissolved in the purified water at room temperature to prepare an aqueous phase. Separately, the preservative and the perfume were dissolved in the ethanol at room temperature to thereby prepare an alcoholic phase. The alcoholic phase was mixed with the aqueous phase, the alkyl-modified carboxyvinylpolymer, and the silicone derivative so as to prepare a microemulsion, to thereby obtain the desired lotion.

Industrial Applicability

As described above, according to the present invention, there are provided: 1. an external-use composition which does not provide a sticky sensation in use, which sensation would otherwise be derived from an ultraviolet absorbent, and an external-use composition which can incorporate an ultraviolet scattering agent, which agent tends to aggregate, in such a manner that the agent is maintained in dispersed state in the composition; 2. an external-use composition which provides superior sensation in use by maintaining a unique sensation due to use of xyloglucan, which composition is also superior in terms of stability under high temperature with the passage of time; 3. an external-use composition which is superior in moisture retention, and provides good fit for the skin, no sticky sensation, and a smooth sensation in use; 4. an external-use composition which provides greatly improved sensation in use and has superior salt tolerance; and 5. an external-use composition which does not provide poor fit for the skin during use even when an alkyl-modified carboxyvinylpolymer is incorporated, which polymer has the advantage of maintaining the composition in stable conditions without incorporation of a surfactant, and the composition having superior salt tolerance. Also, there is provided an external-use composition which provides greatly improved sensation in use. Accordingly, the present invention is useful for providing an improved external-use composition which can satisfy a variety of consumer needs.

What is claimed is:

1. An external-use composition comprising xyloglucan.
2. The external-use composition according to claim 1 which contains an ultraviolet shielding agent.
3. The external-use composition according to claim 2, wherein the ultraviolet shielding agent is a water-soluble ultraviolet absorbent.
4. The external-use composition according to claim 3, wherein the water-soluble ultraviolet absorbent is a sugar-derived ultraviolet absorbent.
5. The external-use composition according to claim 4, further comprising an ultraviolet scattering agent.
6. The external-use composition according to claim 1, further comprising a thickening polysaccharide.
7. The external-use composition according to claim 6, further comprising a surfactant.
8. The external-use composition according to claim 7, wherein the surfactant is a nonionic surfactant.
9. The external-use composition according to claim 7, wherein the surfactant is a sugar-derived surfactant.
10. The external-use composition according to claim 6, wherein the thickening polysaccharide is one or more members selected from the group consisting of hydroxyethyl cellulose, xanthan gum, agar, locust bean gum, and tragacanth gum.
11. The external-use composition according to claim 6, further comprising sericin.
12. The external-use composition according to claim 11, wherein amounts of the xyloglucan, the thickening polysaccharide, and the sericin are as follows:
   (A) xyloglucan: 0.01–5.0% by weight with respect to the entirety of the external-use composition;
   (B) thickening polysaccharide: 0.01–5.0% by weight with respect to the entirety of the external-use composition; and
   (A) sericin: 0.001–5.0% by weight with respect to the entirety of the external-use composition.
13. The external-use composition according to claim 11, wherein the thickening polysaccharide is hydroxyethylcellulose and/or xanthan gum.
14. The external-use composition according to claim 1, further comprising a carboxyvinylpolymer.
15. The external-use composition according to claim 1, further comprising an alkyl-modified carboxyvinylpolymer.
16. The external-use composition according to claim 15, further comprising a silicone derivative.
17. The external-use composition according to claim 16, wherein the silicone derivative is one or more members selected from the group consisting of highly polymerized dimethylpolysiloxanes, highly polymerized amino-modified silicones, and cyclic silicones.
18. The external-use composition according to claim 7, wherein the thickening polysaccharide is one or more members selected from the group consisting of hydroxyethyl cellulose, xanthan gum, agar, locust bean gum, and tragacanth gum.
19. The external-use composition according to claim 8, wherein the thickening polysaccharide is one or more members selected from the group consisting of hydroxyethyl cellulose, xanthan gum, agar, locust bean gum, and tragacanth gum.
20. The external-use composition according to claim 9, wherein the thickening polysaccharide is one or more members selected from the group consisting of hydroxyethyl cellulose, xanthan gum, agar, locust bean gum, and tragacanth gum.
21. The external-use composition according to claim 12, wherein the thickening polysaccharide is hydroxyethylcellulose and/or xanthan gum.
22. The external-use composition according to claim 1, wherein xyloglucan is produced by removing foreign matter from beans of tamarind, dipping the beans in water, crushing, removing impurities from the crushed product, washing and drying the crushed product, and finely cushing the dried product.
23. The external-use composition according to claim 2, in which xyloglucan is contained in an amount of 0.01–10.0 wt %.
24. The external-use composition according to claim 2, in which the ultraviolet shielding agent is an ultraviolet absorbent.
25. The external-use composition according to claim 2, in which the ultraviolet shielding agent is an ultraviolet scattering agent.
26. The external-use composition according to claim 25, in which the ratio of the ultraviolet absorbent to xyloglucan is 2000:1–1:2 by weight.
27. The external-use composition according to claim 26, in which the ratio of the ultraviolet scattering agent to xyloglucan is 800:1–1:2 by weight.

* * * * *